US009642816B2

United States Patent
Alonso Fernández et al.

(10) Patent No.: US 9,642,816 B2
(45) Date of Patent: May 9, 2017

(54) NANOCAPSULES OF PROTAMINE

(71) Applicant: Universidade de Santiago de Compostela, Santiago de Compostela (ES)

(72) Inventors: María José Alonso Fernández, Santiago de Compostela (ES); Noemi Csaba, Santiago de Compostela (ES); José Vicente González Aramundiz, Santiago de Compostela (ES)

(73) Assignee: Universidade de Santiago de Compostela, Santiago de Compostela (ES)

( * ) Notice: Subject to any disclaimer, the term of this patent is extended or adjusted under 35 U.S.C. 154(b) by 0 days.

(21) Appl. No.: 14/653,027

(22) PCT Filed: Dec. 17, 2013

(86) PCT No.: PCT/ES2013/070885
§ 371 (c)(1),
(2) Date: Oct. 13, 2015

(87) PCT Pub. No.: WO2014/096491
PCT Pub. Date: Jun. 26, 2014

(65) Prior Publication Data
US 2016/0038433 A1 Feb. 11, 2016

(30) Foreign Application Priority Data
Dec. 17, 2012 (ES) .................................. 201231956

(51) Int. Cl.
| | |
|---|---|
| G06T 7/00 | (2006.01) |
| G06T 11/60 | (2006.01) |
| A61K 9/51 | (2006.01) |
| A61K 31/337 | (2006.01) |
| A61K 39/145 | (2006.01) |
| A61K 39/29 | (2006.01) |
| C12N 7/00 | (2006.01) |
| A61K 9/19 | (2006.01) |

(52) U.S. Cl.
CPC .......... *A61K 9/5169* (2013.01); *A61K 9/5192* (2013.01); *A61K 31/337* (2013.01); *A61K 39/145* (2013.01); *A61K 39/292* (2013.01); *C12N 7/00* (2013.01); *A61K 9/19* (2013.01); *C12N 2730/10134* (2013.01); *C12N 2760/16134* (2013.01)

(58) Field of Classification Search
CPC ...... A61K 9/5169; A61K 31/337; A61K 9/19; A61K 39/145
See application file for complete search history.

(56) References Cited

U.S. PATENT DOCUMENTS

2014/0023703 A1* 1/2014 Alonso Fernandez .. B82Y 5/00
424/452

FOREIGN PATENT DOCUMENTS

| ES | 2385995 A1 | 8/2012 |
|---|---|---|
| ES | 2386177 A1 | 8/2012 |
| WO | 2012095543 A1 * | 7/2012 |

OTHER PUBLICATIONS

Agarwal et al; title: Stable nanocolloids of poorly soluble drugs with high drug content prepared using the combination of sonication and layer-by-layer technology; Journal of Controlled Release; vol. 128, Issue 3, pp. 255-260, published Jun. 24, 2008.*
Salager, titled: Surfactants types and uses, available 2002.*
US. Food and Drug Administration, title: Protamine Sulfate, downloaded from http://www.accessdata.fda.gov/scripts/cder/drugsatfda/index.cfm?fuseaction=Search.Overview&DrugName=PROTAMINE%20SULFATE on Dec. 5, 2016.*
Gomez Martinez, J. M. et al., "Surface coating of PLGA microparticles with protamine enhances their immulogical performance through facilitated phagocytosis," *Journal of Controlled Release*, vol. 130, pp. 161-167, 2008.
International Search Report for PCT/ES2013/070885 dated Mar. 4, 2014.
Shukla, P. et al., "Emerging trend in nano-engineered polyelectrolyte-based surrogate carriers for delivery of bioactives," *Exp. Opin. Drug. Deliv.*, vol. 7, No. 9, pp. 993-1011, 2010.
Tiourina, O. P. et al.,"Multilayer alginate/protamine microsized capsules: encapsulation of a-chymotrypsin and controlled release study," *International Journal of Pharmaceutics*, vol. 242, pp. 155-161, 2002.
Written Opinion for PCT/ES2013/070885 dated Mar. 4, 2014.

* cited by examiner

*Primary Examiner* — Yanzhi Zhang
(74) *Attorney, Agent, or Firm* — Timothy J. Monahan; Monahan & Company, LLC

(57) ABSTRACT

The present invention relates to the design and development of nanocapsule systems for the administration of active substances, wherein the nanocapsules of the system have a mean diameter less than 1 μm and are characterized by comprising (a) a protamine shell, (b) an oily core, and one or more surfactants characterized by having a hydrophilic-lipophilic ratio greater than 8, provided that said surfactant is not a phospholipid.

22 Claims, 14 Drawing Sheets

NANOCAPSULES OF PROTAMINE

RELATED APPLICATIONS

This application is a 35 U.S.C. §371 national stage filing of International Application No. PCT/ES2013/070885, filed on Dec. 17, 2013, which claims priority to Spanish Patent Application No. P201231956, filed on Dec. 17, 2012. The entire contents of each of the foregoing applications are incorporated herein by reference.

FIELD OF THE ART

The present invention relates to a system for the administration of active substances comprising nanometer-sized protamine-based nanocapsules, as well as to the pharmaceutical compositions comprising same and methods for their preparation.

PRIOR ART

The incorporation of active ingredients in nanometer-sized systems has helped solve the formulation limitations these molecules have, increasing additionally their therapeutic potential. Improvements in solubility, protection against degradation or a greater penetration of the active ingredients are some of the advantages offered by the nanoencapsulation of active molecules or the adsorption thereof in the polymer shell. It is also known that the capacity of these systems to cross external barriers and access the inside of the organism depends both on their size and on their composition. Small-sized particles will increase the degree of delivery with respect to those that are larger: nanosystems less than 1 μm in diameter fit this criterion.

Furthermore, it is possible to coat these nanocapsules with polymer materials. Therefore, a possible polymer material is protamine, which belongs to a family of arginine-rich natural polypeptides which are synthesized in the final spermatid stage of many animals and plants in the spermatogenesis process. Although Friedrich Miescher began studying them in 1868, a great deal of work has been done to characterize this group of strongly basic aliphatic peptides having molecular weight between about 4000-10000 Da.

Protamine has been approved as a pharmaceutical excipient and its main application today is in the sustained release formulation of insulin: NPH (Neutral Protamine Hagedorn), in addition to having a health certificate as an active substance because it is the antidote for heparin intoxications.

There have been many varying studies in which this excipient has been used mainly in combination with liposomes for the release of DNA from inside cells (Gene Ther. 1997. 4, 961-968), conjugated with an oligonucleotide; nanoparticles referred to as proticles (Nucleic Acids Res. 2000. 15; 28(10):E45) for the release of vasoactive intestinal peptide (J Control Release. 2008. 10; 130(2):192-8), taking advantage of their supposed antimicrobial activity (J Antimicrob Chemother. 2008 March; 61(3):651-7), among others.

In the aforementioned studies, given its intrinsic activity, protamine has been widely used and researched for forming complexes with genetic material by means of electrostatic interactions between the high positive charge, given by the arginine groups interacting with the anionic groups of the nucleic acids; hence it can bind to and precipitate DNA within the structures used as vehicles in the administration thereof.

The adjuvant activity of this polypeptide, increasing interleukin 2 and interferon gamma secretion as well as T cell proliferation, has also been demonstrated (J Control Release. 2008; 10; 130(2):161-7).

Nevertheless use thereof is impossible in the formulation of nanocapsules of protamine containing an oily core, since this polypeptide destabilizes oil/water emulsions. Taking this into consideration, it is necessary to design new nanocapsule systems that are not destabilized by protamine and benefit from its properties.

DISCLOSURE OF THE INVENTION

The authors of the present invention have developed a nanocapsule system which incorporates protamine and is not destabilized due to its presence. This nanocapsule system is stable, easy to produce and furthermore allows effectively associating different kinds of both hydrophilic and lipophilic active ingredients. The smaller size of said nanocapsules (less than 1 μm in diameter) and the positive surface charge of protamine allows interaction with negatively charged biological surfaces of the organism, such as the mucosae, and enables them to pass through said surfaces and be internalized by cells. The presence of a polymer shell also provides the nanocapsules with greater stability and beneficial characteristics typical of protamine.

Therefore, a first aspect of the present invention relates to a nanocapsule system (hereinafter "nanocapsule system of the invention") suitable for the administration of active substances, where the nanocapsules of the system comprise:
  a. a surface layer consisting of the polypeptide protamine or comprising the polypeptide protamine;
  b. an oily core;
  c. a surfactant characterized by having a hydrophilic-lipophilic ratio (hydrophilic-lipophilic balance (HLB)) greater than 8; and
  d. optionally at least one active substance,
  provided that the surfactant is not a phospholipid.

Examples of surfactants suitable for putting the present invention into practice are: polyoxyethylene sorbitan monooleate (Tween 80®), polyoxyethylene sorbitan monolaurate (Tween 20®), polyoxyethylene sorbitan monostearate (Tween 61®), polyoxyethylene sorbitan monooleate (Tween 81®), polyoxyethylene sorbitan tristearate (Tween 65®), polyoxyethylene sorbitan trioleate (Tween 85®), polyoxyethylene sorbitan monolaurate (Tween 21®), polyethylene glycol monostearate, polyethylene glycol stearate, polyethylene glycol dilaurate, polyethylene glycol monopalmitate, polyethylene glycol stearate, Poloxamer 124, Poloxamer 188, Poloxamer 237, Poloxamer 338, Poloxamer 407, Solutol HS15®, TPGS, triethanolammonium oleate, sodium oleate, sodium cholate, sodium deoxycholate, sodium lauryl sulfate, iriethanolamine oleate, tragacanth gum and sodium dodecyl sulfate or any combination of the mentioned surfactants. The surfactant is selected from the list consisting of sodium cholate, polyethylene glycol stearate, Solutol HS15 ®, TPGS, polyoxyethylene sorbitan monooleate (Tween 80®) and polyoxyethylene sorbitan monolaurate (Tween 20®) or any combination of these surfactants.

Examples of components of the oily core suitable for putting the present invention into practice are: peanut oil, cottonseed oil, olive oil, castor oil, soybean oil, safflower oil, palm oil, α tocopherol (vitamin E), isopropyl myristate, squalene, Miglyol®, Labrafil®, Labrafac®, Peceol® and Maisine® or any combination of these oils. The oily lipophilic core is preferably selected from the list consisting of Miglyol® (such as Miglyol 812, for example), squalene or α tocopherol or any of their combinations.

In a particular embodiment of the first aspect of the invention, the nanocapsule system of the invention comprises:
a. a surface layer consisting of the polypeptide protamine or comprising the polypeptide protamine;
b. an oily core selected from the list consisting of Miglyol®, squalene or α tocopherol or any of their combinations;
c. a surfactant characterized by having a hydrophilic-lipophilic ratio (hydrophilic-lipophilic balance (HLB)) greater than 8, selected from the list consisting of sodium cholate, polyethylene glycol stearate, Solutol HS15®, TPGS, polyoxyethylene sorbitan monooleate (Tween 80®) and polyoxyethylene sorbitan monolaurate (Tween 20®) or any of their combinations; and
d. optionally at least one active substance.

In another embodiment of the first aspect of present invention, the nanocapsule system of the invention is characterized by being lyophilized.

A second aspect of the invention relates to a method for producing the nanocapsule system of the invention (hereinafter "production method of the invention"). Therefore, in order to achieve the formation of nanocapsules in a desired size range, the method proceeds with the formation of oily cores comprising an oil and one or more surfactants, on the surface of which the coating polymer is bound through different types of interaction. It is therefore of a solvent diffusion process which occurs in a controlled manner and provides stability to the system, without there being a need to create covalent bonds between the components.

Therefore, in a preferred embodiment of the second aspect of the invention, the production method of the invention is a one-step solvent diffusion method comprising the following steps:
a. preparing an aqueous solution comprising protamine;
b. preparing an organic solution comprising the components of the oily core and one or more surfactants characterized by having a hydrophilic-lipophilic ratio greater than 8;
c. mixing the solutions prepared in steps a) and b) under stirring to produce the nanocapsules; and
d. optionally, completely or partially evaporating the organic solvents of the mixture produced in the preceding step to a constant volume, provided that the surfactant is not a phospholipid.

In another preferred embodiment of the second aspect of the invention, the production method of the invention is a two-step solvent diffusion method comprising the following steps:
a. preparing an organic solution comprising the components of the oily core and one or more surfactants characterized by having a hydrophilic-lipophilic ratio greater than 8;
b. adding the solution produced in step a) to an aqueous phase which optionally contains a water-soluble surfactant and is under stirring to form a nanoemulsion;
c. optionally, completely or partially evaporating the organic solvents to a constant volume; and
d. coating the nanoemulsion produced in the preceding step by means of an incubation process with an aqueous solution comprising protamine, provided that the surfactant is not a phospholipid.

In the event that the nanocapsule system of the invention were to comprise an active substance, the method of the invention would include the addition of said active substance to the organic solution if said active substance is lipophilic or to the aqueous solution if said active substance is hydrophilic. The active substances are preferably selected from the list consisting of docetaxel, recombinant hepatitis B antigens (rHBsAg), H1N1 influenza antigens, nucleic acids, saccharide compounds, peptides, proteins or any combination thereof.

A third aspect of the present invention relates to the nanocapsule system of the invention for use in therapy.

In a preferred embodiment of the third aspect of the invention, the nanocapsule system of the invention comprises docetaxel as an active substance, and it is used for the treatment of cancer, preferably lung or pancreatic cancer.

In another preferred embodiment of the third aspect of the invention, the nanocapsule system of the invention comprises recombinant hepatitis B antigen (rHBsAg) as an active substance, and it is used for the treatment or prevention of hepatitis B.

In yet another preferred embodiment of the third aspect of the invention, the nanocapsule system of the invention comprises H1N1 influenza (HI) recombinant antigen as an active substance, and it is used for the treatment or prevention of H1N1-type influenza.

A fourth aspect of the invention relates to a pharmaceutical composition comprising the nanocapsule system of the invention and optionally one or more pharmaceutically acceptable excipients.

DETAILED DISCLOSURE OF THE INVENTION

Figure 1:
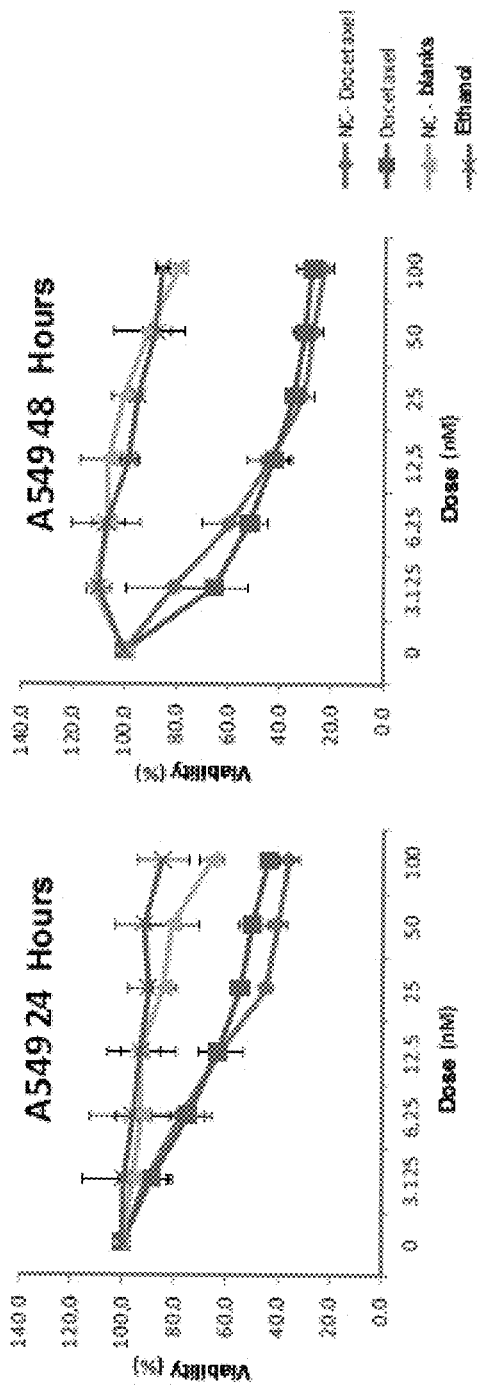
FIG. 1: Viability of the A549 cancer cell line after 24 and 48 hours of contact with nanocapsules of protamine loaded with DCX, blank nanocapsules of protamine, solution of DCX in ethanol and ethanol.
Figure 2:
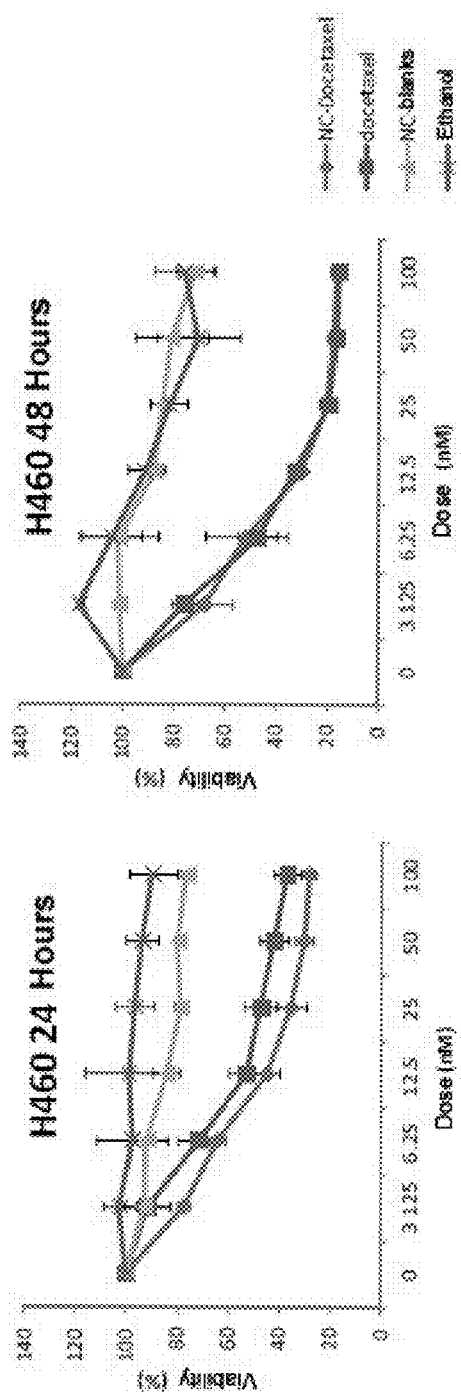
FIG. 2: Viability of the H460 cancer cell line after 24 and 48 hours of contact with nanocapsules of protamine loaded with DCX, blank nanocapsules of protamine, solution of DCX in ethanol and ethanol.
Figure 3:
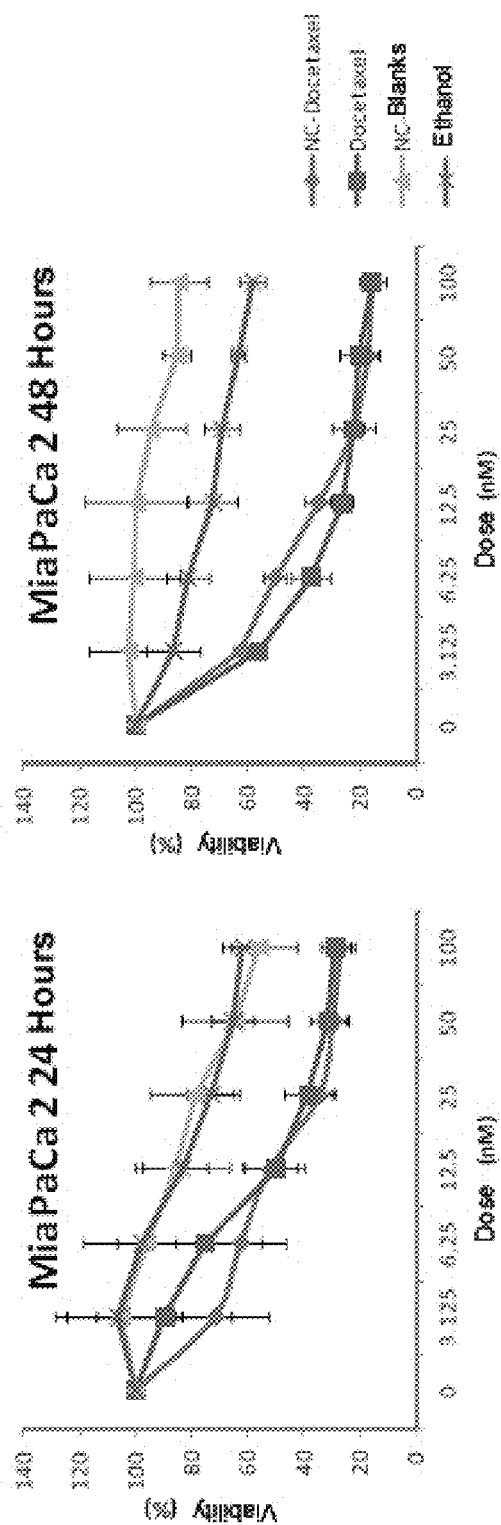
FIG. 3: Viability of the MiaPaCa 2 cancer cell line after 24 and 48 hours of contact with nanocapsules of protamine loaded with DCX, blank nanocapsules of protamine, solution of DCX in ethanol and ethanol.
Figure 4:
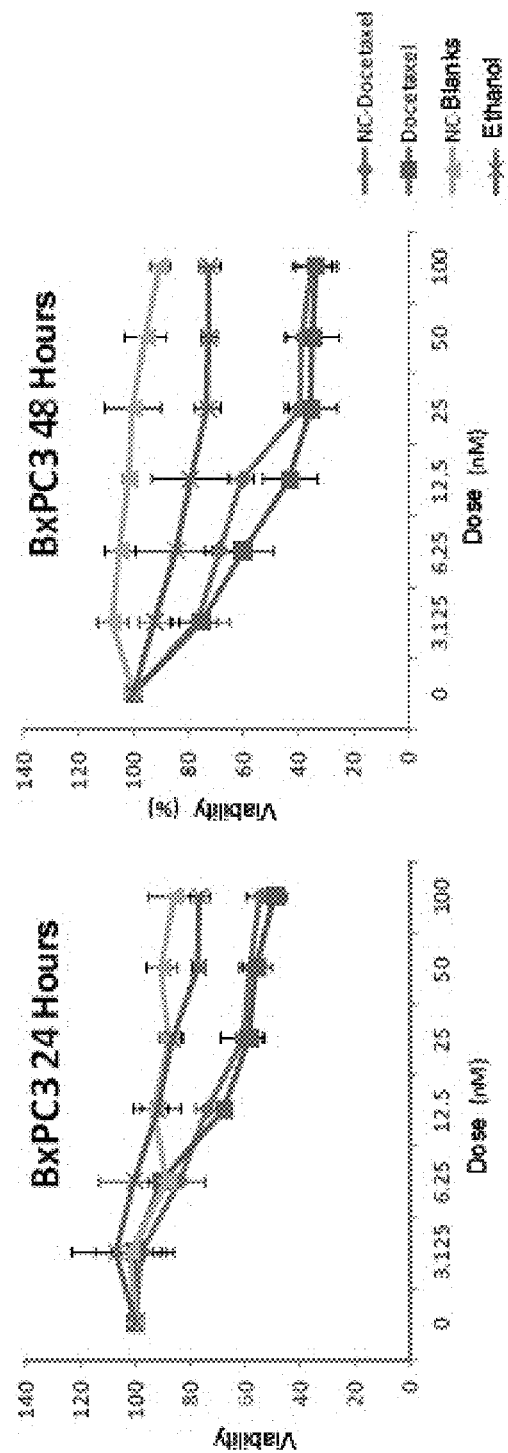
FIG. 4: Viability of the BxPC3 cancer cell line after 24 and 48 hours of contact with nanocapsules of protamine loaded with DCX, blank nanocapsules of protamine, solution of DCX in ethanol and ethanol.

The present invention relates to the design and development of nanocapsule systems for the administration of active substances, wherein the nanocapsules of the system have a mean diameter less than 1 μm and are characterized by comprising (a) a protamine shell, (b) an oily core, and one or more surfactants characterized by having a hydrophilic-lipophilic ratio greater than 8, provided that said surfactant is not a phospholipid.

It is known that protamine destabilizes oil/water emulsions. In fact, not even the use of surfactants such as lipoproteins or others having a phospholipid structure, such as lecithin, phosphatidylglycerol, phosphatidylserine, phosphatidylinositol, diphosphatidylglycerol, phosphatidic acid, phosphatidylcholine and phosphatidylethanolamine can stabilize said oil/water emulsions in which protamine is present. This fact is confirmed in Example 1 of the present invention where the authors have tried to form nanocapsule systems with a mean diameter less than 1 μm characterized by comprising (a) a protamine shell and (b) an oily core using phospholipids such as lecithin, modified lecithins or lysophosphatidylcholine as surfactants without any sort of success.

It is therefore impossible to use protamine in formulations of this type. Therefore, and for the purpose of solving this problem, the authors of the present invention have designed new nanocapsule systems that are not destabilized by protamine and benefit from its properties.

In this sense, the authors of the present invention have discovered how the production of systems comprising nanocapsules of protamine characterized by comprising (a) a protamine shell and (b) an oily core can be observed through the use of certain types of surfactants characterized by having a hydrophilic-lipophilic ratio (hydrophilic-lipophilic balance (HLB)) greater than 8, preferably greater than 12. Therefore, Examples 2.1 to 2.18 illustrates how with different surface active agents, oily cores and preparation methods for preparing systems this type can be obtained, provided that the surfactants used are characterized by having an HLB>8 and are not phospholipids. These examples likewise demonstrate the versatility of the system with respect to its physicochemical characteristics.

Therefore, a first aspect of the present invention relates to a nanocapsule system ("nanocapsule system of the invention) suitable for the administration of active substances, which comprises:
  a. a surface layer consisting of the polypeptide protamine or comprising the polypeptide protamine;
  b. an oily core;
  c. a surfactant characterized by having a hydrophilic-lipophilic ratio (hydrophilic-lipophilic balance (HLB)) greater than 8; and
  d. optionally at least one active substance, provided that the surfactant is not a phospholipid.

The advantage of this specific system of nanocapsules with respect to other systems that are known whether they are nanocapsule or nanoemulsion systems is the presence of the polypeptide protamine in the shell. This polypeptide provides, among other properties, stability to the nanocapsule as well as protection, penetration capacity and specificity in its interaction with given target cells. The presence of protamine on the surface of the nanocapsules furthermore provides greater response by immune cells as they have verified adjuvant activity. Protamine is a natural compound which is advantageous with respect to other polymers with a high content in arginines, such as polyarginine, for example, which is a synthetic molecule. The presence of protamine thereby allows the nanocapsules of the invention to be a safe vehicle that can be rapidly metabolized and excreted, which thereby prevents reaching toxic concentrations and accumulation in the organism. Furthermore, with a protamine shell neither a cryoprotectant for lyophilization nor high dilutions for preventing unwanted aggregation are required for the nanocapsules of the invention.

Additionally, it should be observed that in the context of the present invention the term protamine includes water-soluble protamine salts as well as water-soluble protamine derivatives.

Furthermore, compared to other systems such as liposomes or nanoparticles, which are generally conditioned to a limited drug load, the nanocapsules of the present invention have a higher loading possibility, particularly for lipophilic drugs, due to the presence of the oily core. Another one of the enormous advantages of the nanocapsules of the present invention is the capacity to combine different types of drugs, being able to be a lipophilic drug encapsulated in the core and a hydrophilic drug associated with the shell; the shell likewise offers them stability, protection and specificity.

These systems furthermore have advantages with respect to other larger sized systems (microparticles, pellets, films, sponges . . . ) as regards their biological applications. In fact, it is known that the interaction of a drug release system with a biological surface is highly conditioned by its size. Therefore, the nanocapsules can cross mucosae and be internalized by cells acting as drug delivery systems, whereas microparticles do not have that ability. Likewise, the biodistribution of these systems is highly conditioned by size. The knowledge generated in recent years in the world of nanomedicine and drug release nanosystems has allowed setting up a clearly defined border between the nanometer systems (having a size less than one micron, e.g. nanoparticles and nanocapsules) and the micrometer systems (microparticles and microcapsules). In addition to the behavioral differences as regards their capacity to be internalized by cells and to surpass complex biological barriers, in the case of formulations intended for the intravenous administration of antitumor drugs, the nanometer size of release systems is essential for the purpose of preventing obstruction of blood capillaries. It is likewise known that the possibilities of nanosystems reaching tumor tissue are strictly related to their size and also due to the hydrophilic nature of their surface.

It is likewise important to stress the difference between nanocapsule systems and "complexes". "Complexes" are understood as the nanostructure formed by the interaction of polyelectrolytes or polyelectrolytes and oppositely-charged surfactants. The nanocapsule systems of the present invention differ from complexes in that they are a reservoir-type nanocapsule carrier system in the core of which there can be housed an important number of molecules having more or less affinity for the oily core (encapsulation), and in the shell of which there can be incorporated hydrophilic molecules having a certain affinity for same (adsorption). These characteristics allow maintaining nanostructure integrity and functionality, as well as contribute to a higher stability in the presence of biological fluids.

Therefore, the nanocapsule system of the invention has advantages compared to other drug administration and/or release systems, due to its unique behavior as regards:

- the encapsulation/association of active substances: the system can include one or more hydrophilic or lipophilic active substances or adjuvant substances in proportions greater than the proportions of the nanoparticles, micelles, complexes, nanogels.
- the release of the active substance: the shell plays a role in the rate of release of said substance, allowing the controlled release of the active substance according to the application and needs.
- stability in biological fluids: the polymer shell provides enormous stability to the oily cores, which is advantageous compared to other micro- and nanoemulsion systems.
- the specific interaction with given biological surfaces: the polymer shell provides the oily cores with the possibility to interact with mucosal surfaces as well as with epithelia and specific cells.
- rapid metabolization and excretion of protamine provides this system with a pharmacokinetic safety profile, not being able to demonstrate the same profile for other nanocapsule systems with another type of shell, such as that of polyarginine.
- stability during lyophilization: neither cryoprotectants for the lyophilization process nor high dilutions for preventing unwanted aggregation are required in the nanocapsules of the invention.

The nanocapsules of the system of the present invention have a mean diameter less than 1 μm, therefore corresponding to the definition of nanosystem, a colloidal system based on polymers with a size less than 1 μm, i.e., they have a size of between 1 and 999 nm, preferably between 30 and 500 nm. Mean diameter is understood as the diameter measured by means of the Dynamic Light Scattering (DLS) technique, which is defined by the hydrodynamic diameter of a sphere which scatters at the same speed as the particles being measured. The size of the nanocapsules is primarily influenced by the composition and formation conditions and can be measured using standard methods known by the person skilled in the art and described in the examples section. In this sense, as can be verified the size thereof does not noticeably change when modifying the shell compound ratio in the formulation, nanometer-sized systems being obtained in all cases.

The nanocapsule systems herein described have suitable stability both in suspension and in the lyophilized form. In turn, stability studies seem to indicate that after their administration to human or animal organisms, they do not experience a rapid aggregation or destruction process, but rather they foreseeably remain in nanocapsule form until reaching the target tissue or cell.

On the other hand, as already mentioned the nanocapsule system of the present invention comprises at least one surfactant. In the present invention, the term "surfactant" refers to a component having functional groups and/or structures that allow them to simultaneously interact with the lipophilic and hydrophilic part of the formulation. To prepare the nanocapsule system of the invention, it is necessary to take into consideration the HLB of the surfactant to be used. The concept of HLB is based on an experimental method consisting of attributing a certain HLB number to emulsifying agents based on data relating to the stability of an emulsion. This HLB number implicitly represents several parameters and accounts for the hydrophilic-lipophilic balance of the system. The method for calculating the HLB as it is defined in the present invention is based on the functional groups of the molecule studied, taking into account the force of the hydrophilic groups, it is calculated as follows:

$$HLB=7+m*Hh-n*Hl$$

where m is the number of hydrophilic groups, Hh is the value of the hydrophilic groups, n is the number of lipophilic groups and Hl is their value (Davies, J. T. (1957) "A quantitative kinetic theory of emulsion type. I. Physical chemistry of the emulsifying agent. Gas/Liquid and Liquid/Liquid Interfaces". Proceedings of 2nd International Congress Surface Activity, Butterworths, London, pp. 426-38).

Examples of surfactants suitable for carrying out the present invention are selected from ethoxylated sorbitan esters and fatty acid esters. In a particular embodiment, the sorbitan esters are selected from polyoxyethylene sorbitan monooleate (Tween 80®), polyoxyethylene sorbitan monolaurate (Tween 20®), polyoxyethylene sorbitan monostearate (Tween 61®), polyoxyethylene sorbitan monooleate (Tween 81®), polyoxyethylene sorbitan tristearate (Tween 65®), polyoxyethylene sorbitan trioleate (Tween 85®) and polyoxyethylene sorbitan monolaurate (Tween 21®). In another particular embodiment, the fatty acid esters are selected from polyethylene glycol monostearate, polyethylene glycol stearate, polyethylene glycol dilaurate, polyethylene glycol monopalmitate, polyethylene glycol stearate, Poloxamer 124, Poloxamer 188, Poloxamer 237, Poloxamer 338, Poloxamer 407, Solutol HS15® (polyethylene glycol-15-hydroxystearate), TPGS (D-α-tocopherol polyethylene glycol 1000 succinate). In another particular embodiment, the surfactant is selected from the group consisting of triethanolammonium oleate, sodium oleate, sodium cholate, sodium deoxycholate, sodium lauryl sulfate, triethanolamine oleate, tragacanth gum and sodium dodecyl sulfate. In yet another particular embodiment the surfactant is sodium cholate, polyethylene glycol stearate, TPGS, Solutol HS15®, Tween 20, Tween 80 or combinations thereof.

Poloxamers can be defined as synthetic block copolymers ethylene oxide and propylene oxide (polyoxyethylene-polyoxypropylene), represented by the following general formula:

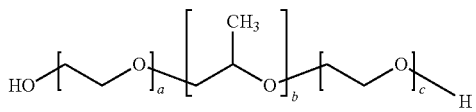

| Type of poloxamer | Ethylene oxide units (a) | Propylene oxide units (b) | Oxyethylene content (percentage) | Mean molecular mass |
| --- | --- | --- | --- | --- |
| 124 | 10-15 | 18-23 | 44.8-48.6 | 2090-2360 |
| 188 | 75-85 | 25-30 | 79.9-83.7 | 7680-9510 |
| 237 | 60-68 | 35-40 | 70.5-74.3 | 6840-8830 |
| 338 | 137-146 | 42-47 | 81.4-84.9 | 12 700-17 400 |
| 407 | 95-105 | 54-60 | 71.5-74.9 | 9840-14 600 |

Optionally, a suitable antioxidant can be added.
(*European Pharmacopoeia* 5.0, pages 2264-2265).

Other examples of surfactants suitable for carrying out the present invention are selected from non-ionic, pharmaceutical-grade surfactants. Non-ionic, pharmaceutical-grade surfactants suitable for carrying out the present invention are preferably selected from the group consisting of long-chain hydroxyl derivatives having from 8 to 18 carbon atoms (fatty alcohols), ethoxylated carboxylic acids, ethoxylated amides, ethoxylated glycerides, glycol esters and derivatives, monoglycerides, polyglyceryl esters, esters and polyalcohol ethers, sorbitol/sorbitan esters, phosphoric acid triesters, ethoxylated fatty alcohol derivatives and polyethylene glycol ethers.

Additionally, the nanocapsule system of the present invention is characterized by having an oily core formed, among other components, from volatile or non-volatile oils. In the context of the present invention, oily core is understood as the core forming the internal structure of the nanocapsules of the invention, and it is made up of at least one oil and at least one surfactant as previously described. These oils can be selected from natural, semi-synthetic and synthetic oils for pharmaceutical use, such as oils from a plant or animal origin, hydrocarbon oils or silicone oils. Oils suitable for carrying out the present invention include, but are not limited to, mineral oil, squalene oil, flavored oils, silicone oil, essential oils, water-insoluble vitamins, isopropyl stearate, butyl stearate, octyl palmitate, cetyl palmitate, tridecyl behenate, diisopropyl adipate, dioctyl sebacate, menthyl anthranilate, cetyl octanoate, octyl salicylate, isopropyl myristate, neopentyl glycol dicaprate ketols, Cerafilos®, decyl oleate, $C_{12}$-$C_{15}$ alkyl lactates, cetyl lactate, lauryl lactate, isostearyl neopentanoate, myristyl lactate, isocetyl stearoyl stearate, octyldodecyl stearoyl stearate, hydrocarbon oils, isoparaffin, fluid paraffins, isododecane, petroleum jelly, argan oil, rapeseed oil, chili oil, coconut oil, corn oil, cottonseed oil, linseed oil, grape seed oil, mustard oil, olive oil, palm oil, fractionated palm oil, peanut oil, castor oil, pine nut oil, poppy seed oil, pumpkin seed oil, rice bran oil, safflower oil, tea oil, truffle oil, vegetable oil, apricot kernel oil, jojoba oil, macadamia nut oil, wheat germ oil, almond oil, soybean oil, sesame seed oil, hazelnut oil, sunflower oil, hempseed oil, rosewood oil, Kukui nut oil, avocado oil, walnut oil, fish oil, berry oil, allspice oil, juniper oil, seed oil, almond seed oil, anise seed oil, celery seed oil, cumin seed oil, nutmeg seed oil, basil leaf oil, bay leaf oil, cinnamon leaf oil, common sage leaf oil, eucalyptus leaf oil, lemon leaf oil, melaleuca leaf oil, oregano leaf oil, patchouli leaf oil, peppermint leaf oil, pine needle oil, rosemary leaf oil, spearmint oil, tea tree leaf oil, thyme oil, teaberry leaf oil, flower oil, chamomile oil, clary sage oil, clove oil, geranium flower oil, hyssop flower oil, jasmine oil, lavender oil, mauka flower oil, marjoram flower oil, orange flower oil, rose flower oil, ylang-ylang flower oil, bark oil, cassia bark oil, cinnamon bark oil, sassafras bark oil, wood oil, camphor wood oil, cedarwood oil, rosewood oil, sandalwood oil, ginger wood oil, tall oil, castor oil, myrrh oil, peel oil, Bergamot peel oil, grapefruit peel oil, lemon peel oil, lime peel oil, orange peel oil, tangerine peel oil, root oil, valerian oil, oleic acid, linoleic acid, oleyl alcohol, isostearyl alcohol, ethyl oleate, Miglyol® (mixture of decanoyl- and octanoyl glyceride), Labrafil® (oleoyl polyoxyl-6 glycerides), Labrafac® (propylene glycol dicaprylocaprate), Rylo® (mixture of fatty acids), Peceol® (glycerol monooleate) and Maisine® (glycerol monolinoleate), synthetic or semi-synthetic derivatives thereof and combinations thereof. The oil is preferably selected from the list consisting of peanut oil, cottonseed oil, olive oil, castor oil, soybean oil, safflower oil, palm oil, α tocopherol (vitamin E), isopropyl myristate, squalene, Miglyol®, Labrafil®, Labrafac®, Peceol® and Maisine® or mixtures thereof. The oils are more preferably Miglyol® (such as for example Miglyol 812 (caprylic/capric triglyceride)), squalene or α tocopherol.

Other oils suitable for carrying out the present invention are selected from the group comprising oils from the terpene family formed by isoprene units (2-methylbuta-1,3-diene) and sub-divided according to their carbon atoms: hemiterpenes (C5), monoterpenes (C10), sesquiterpenes (C15), diterpenes (C20), sesterterpenes (C25), triterpenes (C30), tetraterpenes (C40, carotenoids) and polyterpenes, vitamin A and squalane.

As defined above, the nanocapsules of the invention also optionally comprise at least one active substance. The term "active substance" relates to any substance which is used in the treatment, cure, prevention or diagnosis of a disease or which is used to improve the physical and mental well-being of human beings and animals. The active substance could be, for example, a drug, an antigen, a vitamin, etc. The nanocapsule systems, object of the present invention, are suitable for incorporating lipophilic or hydrophilic active substances.

In a preferred embodiment, the active ingredients are recombinant hepatitis B surface antigens, influenza (H1N1) antigen and docetaxel.

The proportion of active substance incorporated will depend in each case on the active ingredient to be incorporated, the indication for which it is used and the administration efficiency.

On the other hand, the production methods for producing the nanocapsule systems of the invention are simple methods which prevent drastic conditions such as high temperatures. Furthermore, it is not necessary to perform any type of chemical reaction either for producing them, since as previously indicated the production of the system involves non-covalent interactions. Therefore, the integrity of the molecules incorporated in the system, which are susceptible to degradation, is thus preserved. In order to achieve the formation of nanocapsules in a desired size range, the method proceeds with the formation of the oily cores comprising an oil and one or more surfactants, on the surface of which the coating polymer is bound through different types of interaction. It is therefore a solvent diffusion process which occurs in a controlled manner and provides stability to the system, without there being a need to create covalent bonds between the components.

A particular method for producing the systems of the invention (referred to as one-step solvent diffusion method in the examples), comprises:
a) preparing an aqueous solution comprising protamine, and optionally a water-soluble surfactant;
b) preparing an organic solution comprising an oil and one or more surfactants characterized by having a hydrophilic-lipophilic ratio greater than 8, provided that the surfactant is not a phospholipid;
c) mixing the solutions prepared in steps a) and b) under stirring, the nanocapsules being produced spontaneously; and
d) optionally, completely or partially evaporating the organic solvents of the mixture produced in the preceding step to a constant volume.

The systems of the present invention can be prepared by means of an alternative method (referred to as a two-step solvent diffusion method in the examples) which comprises coating a nanoemulsion with protamine by means of an incubation process with an aqueous solution of the polymer. Likewise, the formation of the nanoemulsion can be favored by means of ultrasounds (referred to as sonication method in the examples) or homogenization (referred to as homogenization method in the examples).

In a particular embodiment, the incubation process comprises mixing the nanoemulsion with an aqueous solution of the coating polymer. Said nanoemulsion consists of at least an oil, one or more surfactants characterized by having a hydrophilic-lipophilic ratio greater than 8, and an aqueous phase. The aqueous phase can contain other surfactant agents, salts, and other auxiliary agents.

Preparation methods for preparing said nanoemulsion are known in the state of the art and can comprise a diffusion, sonication or homogenization process (Prego et al. J. Nanosci. Nanotechnol. (2006) 6:1; Tadros et al. Adv. Colloid Interface Sci. (2004) 109:303).

A particular method for producing the nanoemulsion (referred to as solvent diffusion method in the examples) comprises:
i) preparing an organic solution comprising an oil, one or more surfactants characterized by having a hydrophilic-lipophilic ratio greater than 8, provided that the surfactant is not a phospholipid;
ii) adding the solution produced in step i) to an aqueous phase which optionally contains a water-soluble surfactant and is under stirring to form a nanoemulsion;
iii) optionally, completely or partially evaporating the organic solvents to a constant volume.

Another particular method for producing the nanoemulsion (referred to as sonication method in the examples) comprises:
i) preparing an organic solution comprising an oil, one or more surfactants characterized by having a hydrophilic-lipophilic ratio greater than 8, provided that the surfactant is not a phospholipid;
ii) adding the solution produced in step i) to an aqueous phase optionally containing a water-soluble surfactant and sonicating;
iii) diluting the emulsion produced in step ii) with water;
iv) optionally, completely or partially evaporating the organic solvents to a constant volume.

Yet another particular method for producing the nanoemulsion (referred to as in the examples homogenization method) comprises:
i) preparing an organic solution comprising an oil, one or more surfactants characterized by having a hydrophilic-lipophilic ratio greater than 8, provided that the surfactant is not a phospholipid;
ii) adding the solution produced in step i) to an aqueous phase optionally containing a water-soluble surfactant and homogenizing;
iii) diluting the emulsion produced in step ii) with water and homogenizing;
iv) optionally, completely or partially evaporating the organic solvents to a constant volume.

According to particular embodiments of the preceding methods, if the active substance is lipophilic or amphiphilic, said active ingredient is added to the organic solution of step b) or step i). According to other particular embodiments, if the active ingredient is hydrophilic, said active ingredient is added to the solution of step a) or step ii). Said hydrophilic active ingredient is preferably added dissolved in an aqueous solution. It is also possible to incorporate the hydrophilic active ingredient by means of adsorption to the nanocapsule suspension produced in step d) or after the incubation process once the nanocapsules are formed.

Another particular method for producing the nanoemulsion (referred to as variation of the solvent diffusion method (by dripping) in the examples) comprises:
i) preparing an aqueous solution comprising protamine, and optionally a water-soluble surfactant;
ii) preparing an oily phase comprising an oil and one or more surfactants characterized by having a hydrophilic-lipophilic ratio greater than 8, provided that the surfactant is not a phospholipid;
iii) adding the solution produced in step ii) or the aqueous solution produced in step i), in aliquots, at given time intervals to the aqueous solution produced in step i), or to the solution produced in step ii), respectively;
iv) optionally, completely or partially evaporating the organic solvents to a constant volume.

According to particular embodiments of the preceding method, if the active substance is lipophilic or amphiphilic, said active ingredient is added to the organic solution of step ii). According to other particular embodiments, if the active ingredient is hydrophilic, said active ingredient is added to the solution of step i). Said hydrophilic active ingredient is preferably added dissolved in an aqueous solution. It is also possible to incorporate the hydrophilic active ingredient by means of adsorption to the nanocapsule suspension or after the incubation process once the nanocapsules are formed.

In the context of the present invention, lipophilic is understood as those molecules, substances, active substances, structures or part of same that cannot interact by themselves with water molecules and are mainly dissolved in apolar solvents.

In the context of the present invention, amphiphilic is understood as those molecules, substances, active substances, structures or part of same having both hydrophobic and hydrophilic properties.

In the context of the present invention, hydrophilic is understood as those molecules, substances, active substances, structures or part of same that are attracted by water and can be dissolved in water or in polar solvents The formation of the nanocapsules takes place when mixing volumes of the mentioned solutions containing the nanoemulsion with aqueous solutions of the coating polymer in different proportions, changing the coating polymer ratio.

The solvent of the organic solution is preferably a mixture of polar solvents such as ethanol, isopropanol and acetone, furthermore being able to include non-polar solvents such as dichloromethane, for example. The oil and the surfactant or surfactants characterized by having a hydrophilic-lipophilic ratio greater than 8 are incorporated in this organic phase. The active ingredient is likewise incorporated in a particular composition.

A particular example for producing the nanocapsule systems of the invention comprising protamine following the first method described above comprises:

a) preparing 20 ml of an aqueous solution containing 0.05% w/v protamine;
b) preparing an oily phase made up of an ethanol/acetone solution, one or both surfactants (sodium cholate and/or PEG stearate), to which Miglyol® 812 is added.
c) mixing the solutions resulting from steps a) and b) under stirring, the nanocapsules being produced spontaneously;
d) optionally, evaporating the organic solvents of the mixture produced in the preceding step to a constant volume.

The preparation method for preparing the nanocapsule systems can include an additional lyophilization step for the purpose of preserving them during storage so that they conserve their initial characteristics. Due to the nature of the shell of the nanocapsules of the present invention, as well as the characteristics thereof, it is not necessary to use cryoprotectants during lyophilization. Another additional advantage is that it is not necessary to dilute the colloidal system before lyophilization, since the nanocapsule systems of the invention do not form aggregates during lyophilisate reconstitution.

Alternatively, it is possible to add one or more sugars which have a cryoprotectant effect, such as, for example, trehalose, glucose, sucrose, mannitol, maltose, polyvinyl pyrrolidone (PVP). In lyophilized form, the nanocapsules can be stored for long periods of time and be readily regenerated, if needed, by simply adding an optimal volume of water.

According to this additional step, the present invention also relaters to nanocapsule systems comprising a protamine shell in the form of a lyophilisate.

In a particular embodiment, the invention additionally relates to the nanocapsule system of the invention for use in therapy. More specifically, it relates to a pharmaceutical composition comprising the nanocapsule systems of the invention and optionally one or more pharmaceutically acceptable excipients. Particularly, the incorporation of active substances in the nanocapsules of the invention leads to systems the characteristics of which as regards their composition, properties and morphology, make them excellent candidates for the area of therapeutics. The active substance to be incorporated in the systems of the invention will be that substance with pharmacotherapeutic properties that are suitable according to the therapeutic application for which the formulation is intended. In a particular embodiment, the active substance is selected from peptides, proteins, lipid or lipophilic compounds, saccharide compounds, compounds of nucleic acids or nucleotides, such as oligonucleotides, polynucleotides, or combinations of the mentioned molecules.

In a preferred embodiment, the lipophilic active substance is docetaxel.

In another preferred embodiment, the active substance is hydrophobic, amphiphilic or hydrophilic. Hydrophobic or amphiphilic active substances are preferably added in step b) of the preparation method for preparing nanocapsules of the invention. Hydrophilic active substances are preferably added in step a) of the method or in a step after step d) by means of an incubation process. However, the invention also contemplates other embodiments such as, for example, adding in step b) a hydrophilic active substance dissolved in a small volume of aqueous phase. unlike hydrophobic active substances, which are encapsulated within the nanocapsules, hydrophilic active substances can be associated with the surface thereof by means of adsorption.

In a preferred embodiment, the hydrophilic active substances are the recombinant hepatitis B surface antigen and the influenza (H1N1) antigen.

Said pharmaceutical compositions can be administered in different administration routes, such as mucosal, topical or parenteral administration.

The proportion of active substance incorporated in the systems can be up to about 50% by weight with respect to the total dry base weight, of the components of the nanocapsule system. However, the suitable proportion will depend in each case on the active ingredient to be incorporated, the indication for which it is used and the administration efficiency. In a particular embodiment, the proportion of lipophilic active substance can reach up to about 10% by weight, preferably up to about 5%.

As described above, it is possible for the nanocapsule systems described in the present invention to incorporate more than one active substance, which could be dissolved in the same solution or in separate solutions, this depending on the nature of the molecules to be incorporated, preventing the existence of any type of either a chemical or physical interaction between them.

As defined above, the invention relates to the use of said system in the preparation of a medicinal product. In a particular embodiment, said use relates to the use of vaccines or the treatment of cancer. In this sense, in a preferred embodiment of the invention, the nanocapsule system of the invention comprises docetaxel as an active substance and is used for the treatment of cancer, preferably lung or pancreatic cancer. Alternatively, the present invention also relates to the use of the nanocapsule system of the invention comprising docetaxel as an active substance for preparing a medicinal product for the treatment of cancer, preferably lung or pancreatic cancer.

In another preferred embodiment of the invention, the nanocapsule system of the invention comprises recombinant hepatitis B antigen (rHBsAg) as an active substance and is used for the treatment or prevention of hepatitis B. Alternatively, the present invention also relates to the use of the nanocapsule system of the invention comprising recombinant hepatitis B antigen (rHBsAg) as an active substance for preparing a medicinal product for the treatment or prevention of hepatitis B.

In yet another preferred embodiment of the invention, the nanocapsule system of the invention comprises H1N1 influenza (HI) recombinant antigen as an active substance and is used for the treatment or prevention of H1N1-type influenza. Alternatively, the present invention also relates to the use of the nanocapsule system of the invention comprising H1N1 influenza (HI) recombinant antigen as an active substance for preparing a medicinal product for the treatment or prevention of H1N1 influenza.

In order to better understand the features and advantages of the present invention, reference will be made below to a series of examples which, in a descriptive manner, complete the preceding description without said description being limited by these examples in any way.

EXAMPLES

The meaning of the abbreviations used throughout the examples is indicated below.
1. Pr: Protamine; the salt used in the following examples was protamine sulfate (Yuki Gosei Kogyo Co, Ltd.). Another protamine salt (SIGMA) was used without there being significant differences for any of the examples.
2. PEG: polyethylene glycol stearate. Simulsol® M52 PEG-2000 (Seppic).
3. Nanoemulsion (NE): This term is used for the sake of simplicity in the examples to refer to nanosystems comprising an oil and one or more surfactants having an HLB greater than 8; preferably the surfactant or surfactants used were: sodium cholate, PEG stearate, Solutol HS15®, TPGS, Tween 20® and Tween 80® or combination thereof. The only difference with the nanocapsules is the absence of protamine in the coating of the surface of the systems.
4. Nanocapsules (NCs) of Pr=This term is used for the sake of simplicity in the examples and drawings to refer to nanosystems the nanocapsules of which comprise an oil, one or more surfactants having an HLB greater than 8; preferably the surfactant or surfactants used were: sodium cholate, PEG stearate, Solutol HS15®, TPGS, Tween 20, Tween 80 or combination thereof. Finally the coating of Pr.
5. DCX: Docetaxel.
6. rHBsAg: Recombinant hepatitis B antigen.
7. HI: H1N1 influenza antigen
8. Miglyol®: Miglyol 812

Example 1

Example 1.1

Nanocapsules of protamine consisting of an oily Miglyol® core were prepared according to the one-step solvent diffusion method:
i) an aqueous solution (10 ml) in which protamine is dissolved at a concentration of 0.05 w/v was prepared.
ii) an oily phase made up of an ethanol/acetone solution (0.25:4.5 ml), 62.5 µl of Miglyol® and 15 mg of phospholipids (lecithin, lysophosphatidylcholine, hydroxylated lecithin Yelkin®, oil-free lecithin Ultralec®) was prepared.

iii) the solutions resulting from steps i) and ii) were mixed under magnetic stirring for 10 minutes, the nanocapsules being produced spontaneously.
iv) the organic solvents were evaporated to a constant volume.

Once prepared, their mean diameter, polydispersion index (PI) as well as their surface electric charge (zeta-potential) were measured. Table 1 shows the values obtained for the mentioned parameters:

TABLE 1

| Formulation | Phospholipid | Size (nm) | PI | Z-potential (nm) |
|---|---|---|---|---|
| NC Pr | Lecithin | | | Aggregates |
| NC Pr | Lysophosphatidylcholine | | | Aggregates |
| NC Pr | Hydroxylated lecithin | | | Aggregates |
| NC Pr | Oil-free lecithin | | | Aggregates |

Example 1.2

Nanocapsules of protamine consisting of an oily Miglyol® core were prepared according to the two-step solvent diffusion method:
i) an oily phase made up of an ethanol/acetone solution (0.25:4.5 ml), 62.5 µl of Miglyol® and different amounts of phospholipids (lecithin or lysophosphatidylcholine) was prepared.
ii) the solution produced in step i) was added to 10 ml of an aqueous solution under magnetic stirring and kept therein for 10 minutes, the nanoemulsion is thereby produced spontaneously.
iii) the organic solvents were evaporated to a constant volume.
iv) the nanoemulsion produced in step iii) was coated by means of an incubation process with an aqueous solution (1 ml) made up of Pr at a concentration of 1 or 2 mg/ml, in a proportion of 1:1 and 1:2 (ml of nanoemulsion:mg of Pr), the coating being produced immediately regardless of the temperature.

Once prepared, their mean diameter, polydispersion index (PI) as well as their surface electric charge (zeta-potential) were measured. Table 2 shows the values obtained for the mentioned parameters according to the amount of phospholipids and different protamine ratios in step iv).

TABLE 2

| Formulation | Phospholipid | Amount of phospholipid (mg) | Pr step iv (mg) | Size (nm) | PI | Z-potential (nm) |
|---|---|---|---|---|---|---|
| NC Pr | lecithin | 15 | 1 | | | Aggregates |
| NC Pr | | | 2 | | | Aggregates |
| NC Pr | | 30 | 1 | | | Aggregates |
| NC Pr | | | 2 | | | Aggregates |
| NC Pr | lysophosphatidylcholine | 15 | 1 | | | Aggregates |
| NC Pr | | | 2 | | | Aggregates |

Example 1.3

Nanocapsules of protamine consisting of an oily Miglyol® core were prepared according to the one-step solvent diffusion method:

i) an aqueous solution (10 ml) in which protamine is dissolved at a concentration of 0.05 w/v was prepared.
ii) an oily phase made up of a dichloromethane/acetone solution (at ratios of 0.1:4.5 ml to 0.25:4.5 ml), 62.5 μl of Miglyol® and an amount of hydroxylated lecithin (Yelkin®) or oil-free lecithin (Ultralec®) was prepared.
iii) the solutions resulting from steps i) and ii) were mixed under magnetic stirring for 10 minutes, the nanocapsules being produced spontaneously.
iv) the organic solvents were evaporated to a constant volume.

Once prepared, their mean diameter, polydispersion index (PI) as well as their surface electric charge (zeta-potential) were measured. Table 1 shows the values obtained for the mentioned parameters:

TABLE 1

| Formulation | Phospholipid | Mg of lecithin | Size (nm) | PI | Z-potential (nm) |
|---|---|---|---|---|---|
| NC Pr | Hydroxylated | 15 | | | Aggregates |
| NC Pr | lecithin | 30 | | | Aggregates |
| NC Pr | Oil-free lecithin | 15 | | | Aggregates |
| NC Pr | | 30 | | | Aggregates |

Example 1.4

Nanocapsules of protamine consisting of an oily Miglyol® core were prepared according to the two-step solvent diffusion method:

i) an oily phase made up of a dichloromethane/acetone solution (at ratios of 0.1:4.5 ml to 0.25:4.5 ml), 62.5 μl of Miglyol® and different amounts of phospholipids (hydroxylated lecithin or oil-free lecithin) was prepared.
ii) the solution produced in step i) was added to 10 ml of an aqueous solution under magnetic stirring and kept therein for 10 minutes, the nanoemulsion is thereby produced spontaneously.
iii) the organic solvents were evaporated to a constant volume.
iv) the nanoemulsion produced in step iii) was coated by means of an incubation process with an aqueous solution (1 ml) made up of Pr at a concentration of 1 or 2 mg/ml, in a proportion of 1:1 and 1:2 (ml of nanoemulsion:mg of Pr), the coating being produced immediately regardless of the temperature.

Once prepared, their mean diameter, polydispersion index (PI) as well as their surface electric charge (zeta-potential) were measured. Table 2 shows the values obtained for the mentioned parameters according to the amount of phospholipids and different protamine ratios in step iv).

TABLE 2

| Formulation | Phospholipid | Amount of phospholipid (mg) | Pr step iv (mg) | Size (nm) | PI | Z-potential (nm) |
|---|---|---|---|---|---|---|
| NC Pr | Hydroxylated | 15 | 1 | | | Aggregates |
| NC Pr | lecithin | | 2 | | | Aggregates |
| NC Pr | | 30 | 1 | | | Aggregates |
| NC Pr | | | 2 | | | Aggregates |
| NC Pr | Oil-free lecithin | 15 | 1 | | | Aggregates |
| NC Pr | | | 2 | | | Aggregates |
| NC Pr | | 30 | 1 | | | Aggregates |
| NC Pr | | | 2 | | | Aggregates |

Example 2

Example 2.1

Nanocapsules of protamine consisting of an oily Miglyol® core were prepared according to the one-step solvent diffusion method:

i) an aqueous solution (10 ml) in which Pr is dissolved at a concentration of 0.05 w/v was prepared. Additionally, this solution can have 0.25% w/v of Poloxamer 188.
ii) an oily phase made up of an ethanol/acetone solution (0.25:4.5 ml), 62.5 μl of Miglyol®, 40 mg of sodium cholate and 48 mg of PEG stearate was prepared.
iii) the solutions resulting from steps i) and ii) were mixed under magnetic stirring for 10 minutes, the nanocapsules being produced spontaneously.
iv) the organic solvents were evaporated to a constant volume.

Once prepared, their mean diameter, polydispersion index (PI) as well as their surface electric charge (zeta-potential) were measured. Table 3 shows the values obtained for the mentioned parameters:

TABLE 3

| Formulation | Poloxamer 188 | Size (nm) | PI | Z-potential (mv) |
|---|---|---|---|---|
| NC Pr | NO | 227 ± 6 | 0.139 | +20 ± 2 |
| NC Pr | Yes | 229 ± 20 | 0.153 | +16 ± 2 |

Example 2.2

Nanocapsules of protamine consisting of an oily Miglyol® core were prepared according to the two-step solvent diffusion method:

i) an oily phase made up of an ethanol/acetone solution (0.25:4.5 ml), 62.5 μl of Miglyol®, 40 mg of sodium cholate and 48 mg of PEG stearate was prepared.
ii) the solution produced in step i) was added to 10 ml of an aqueous solution under magnetic stirring and kept therein for 10 minutes, the nanoemulsion is thereby produced spontaneously:
iii) the organic solvents were evaporated to a constant volume.
iv) the nanoemulsion produced in step iii) was coated by means of an incubation process with an aqueous solution (1 ml) made up of Pr at a concentration of 1 or 2 mg/ml, in a proportion of 1:1 and 1:2 (ml of nanoemulsion:mg of protamine), the coating being produced immediately regardless of the temperature.

Once prepared, their mean diameter, polydispersion index (PI) as well as their surface electric charge (zeta-potential) were measured. Table 4 shows the values obtained for the mentioned parameters according to the amount of Pr in step iv).

TABLE 4

| Formulation | Size (nm) | PI | Z-potential (mv) |
|---|---|---|---|
| NC Pr (1 ml of NE per 1 mg peptide) | 206 ± 2 | 0.095 | +22 ± 2 |
| NC Pr (1 ml of NE per 2 mg peptide) | 210 ± 3 | 0.074 | +25 ± 6 |

Example 2.3

Nanocapsules of protamine consisting of an oily α tocopherol core and different amounts of PEG-stearate were prepared according to the one-step solvent diffusion method:
  i) an aqueous solution (10 ml) in which protamine is dissolved at a concentration of 0.05 mg/ml was prepared.
  ii) an oily phase made up of an ethanol/acetone solution (0.25:4.5 ml), 60 mg of α tocopherol and different amounts of PEG-stearate was prepared.
  iii) the solutions resulting from steps i) and ii) were mixed under magnetic stirring for 10 minutes, the nanocapsules being produced spontaneously.
  iv) the organic solvents were evaporated to a constant volume.

Once prepared, their mean diameter, polydispersion index (PI) as well as their surface electric charge (zeta-potential) were measured. Table 5 shows the values obtained for the mentioned parameters according to the amount of PEG-stearate.

TABLE 5

| Formulation | PEG step ii (mg) | Size (nm) | PI | Z-potential (mV) |
|---|---|---|---|---|
| NC Pr | 48 | 214 ± 15 | 0.2 | +1 ± 2 |
| NC Pr | 24 | 214 ± 31 | 0.2 | +9 ± 5 |
| NC Pr | 12 | 234 ± 5 | 0.2 | +17 ± 4 |

Example 2.4

Nanocapsules of protamine consisting of an oily α tocopherol core were prepared according to the two-step solvent diffusion method:
  i) an oily phase made up of an ethanol/acetone solution (0.25:4.5 ml), 60 mg of α tocopherol and different amounts of PEG-stearate was prepared.
  ii) the solution produced in step i) was added to 10 ml of an aqueous solution under magnetic stirring and kept therein for 10 minutes, the nanoemulsion is thereby produced spontaneously:
  iii) the organic solvents were evaporated to a constant volume.
  iv) the nanoemulsion produced in step iii) was coated by means of an incubation process with an aqueous solution (1 ml) made up of Pr at a concentration of 1 or 2 mg/ml, in a proportion of 1:1 and 1:2 (ml of nanoemulsion:mg of protamine), the coating being produced immediately regardless of the temperature.

Once prepared, their mean diameter, polydispersion index (PI) as well as their surface electric charge (zeta-potential) were measured. Table 6 shows the values obtained for the mentioned parameters according to the amount of PEG-stearate and different protamine ratios in step iv).

TABLE 6

| Formulation | PEG step i (mg) | Pr step iv (mg) | Size (nm) | PI | Z-potential (nm) |
|---|---|---|---|---|---|
| NC Pr | 48 | 1 | 205 ± 10 | 0.1 | +4 ± 3 |
| NC Pr |    | 2 | 210 ± 15 | 0.2 | +6 ± 9 |
| NC Pr | 24 | 1 | 205 ± 9  | 0.1 | +17 ± 5 |
| NC Pr |    | 2 | 216 ± 17 | 0.2 | +4 ± 2 |
| NC Pr | 12 | 1 | 226 ± 7  | 0.2 | +16 ± 9 |
| NC Pr |    | 2 | 238 ± 18 | 0.2 | +9 ± 6 |

Example 2.5

Nanocapsules of protamine consisting of an oily squalene core and different amounts of surfactants were prepared according to the one-step solvent diffusion method:
  i) an aqueous solution (10 ml) in which protamine is dissolved at a concentration of 0.05 w/v was prepared.
  ii) an oily phase made up of an acetone solution (4.75 ml), 62.5 μl of squalene and different amounts of PEG-stearate was prepared.
  iii) the solutions resulting from steps i) and ii) were mixed under magnetic stirring for 10 minutes, the nanocapsules being produced spontaneously.
  iv) the organic solvents were evaporated to a constant volume.

Once prepared, their mean diameter, polydispersion index (PI) as well as their surface electric charge (zeta-potential) were measured. Table 7 shows the values obtained for the mentioned parameters according to the amount of PEG-stearate:

TABLE 7

| Formulation | PEG step ii (mg) | Size (nm) | PI | Z-potential (mV) |
|---|---|---|---|---|
| NC Pr | 48 | 235 ± 4 | 0.2 | −3 ± 3 |
| NC Pr | 12 | 250 ± 6 | 0.2 | +11 ± 5 |

Example 2.6

Nanocapsules of protamine consisting of an oily squalene core were prepared according to the two-step solvent diffusion method:
  i) an oily phase made up of an acetone solution (4.5 ml), 62.5 μl of squalene and different amounts of PEG-stearate was prepared.
  ii) the solution produced in step i) was added to 10 ml of an aqueous solution under magnetic stirring and kept therein for 10 minutes, the nanoemulsion is thereby produced spontaneously:
  iii) the organic solvents were evaporated to a constant volume.
  iv) the nanoemulsion produced in step iii) was coated by means of an incubation process with an aqueous solution (1 ml) made up of Pr at a concentration of 1 or 2 mg/ml, in a proportion of 1:1 and 1:2 (ml of nanoemulsion:mg of protamine), the coating being produced immediately regardless of the temperature.

Once prepared, their mean diameter, polydispersion index (PI) as well as their surface electric charge (zeta-potential) were measured. Table 8 shows the values obtained for the mentioned parameters according to the amount of PEG-stearate and different protamine ratios in step iv).

TABLE 8

| Formulation | PEG step i (mg) | Pr step iv (mg) | Size (nm) | PI | Z-potential (nm) |
|---|---|---|---|---|---|
| NC Pr | 96 | 1 | 227 ± 2 | 0.2 | +26 ± 1 |
| NC Pr |  | 2 | 228 ± 2 | 0.2 | +10 ± 1 |
| NC Pr | 48 | 1 | 238 ± 5 | 0.2 | +19 ± 2 |
| NC Pr |  | 2 | 232 ± 6 | 0.2 | +0.6 ± 3 |

Example 2.7

Nanocapsules of protamine consisting of an oily α tocopherol core and different surfactants were prepared according to the one-step solvent diffusion method:
i) an aqueous solution (10 ml) in which protamine is dissolved at a concentration of 0.05 w/v was prepared.
ii) an oily phase made up of an ethanol/acetone solution (0.25:4.5 ml), and 3 different α tocopherol ratios was prepared and PEG-stearate (PEG-st) or Solutol HS15 was used as surfactant. The α tocopherol:surface active agent mass ratios were 12:12, 60:12 and 60:60, respectively.
iii) the solutions resulting from steps i) and ii) were mixed under magnetic stirring for 10 minutes, the nanocapsules being produced spontaneously.
iv) the organic solvents were evaporated to a constant volume.

Once prepared, their mean diameter, polydispersion index (PI) as well as their surface electric charge (zeta-potential) were measured. Table 9 shows the values obtained for the mentioned parameters.

TABLE 9

| Surface active agent | PEG-St | | | Solutol HS15 | | |
|---|---|---|---|---|---|---|
| Ratio (oily core:surface active agent) | Size (nm) | PI | Z-potential (mV) | Size (nm) | PI | Z-potential (mV) |
| 12:12 | 218 ± 11 | 0.1 | +6 ± 1 | 146 ± 1 | 0.01 | −1 ± 0.4 |
| 60:12 | 234 ± 5 | 0.2 | +17 ± 4 | 250 ± 39 | 0.3 | 23 ± 5 |
| 60:60 | 203 ± 3 | 0.1 | −4 ± 0.5 | 176 ± 23 | 0.2 | −2 ± 0.5 |

Example 2.8

Nanocapsules of protamine consisting of an oily α tocopherol core and different surfactants were prepared according to the one-step solvent diffusion method:
i) an aqueous solution (10 ml) in which protamine is dissolved at a concentration of 0.05 w/v was prepared.
ii) an oily phase made up of an ethanol/acetone solution (0.25:4.5 ml), and 3 different α tocopherol ratios was prepared and Tween 20 or Tween 80 was used as surfactant. The α tocopherol:surfactant mass ratios were 12:12 and 60:12, respectively
iii) the solutions resulting from steps i) and ii) were mixed under magnetic stirring for 10 minutes, the nanocapsules being produced spontaneously.
iv) the organic solvents were evaporated to a constant volume.

Once prepared, their mean diameter, polydispersion index (PI) as well as their surface electric charge (zeta-potential) were measured. Table 10 shows the values obtained for the mentioned parameters:

TABLE 10

| Surface active agent | Tween 20 | | | Tween 80 | | |
|---|---|---|---|---|---|---|
| Ratio (oily core:surface active agent) | Size (nm) | PI | Z-potential (mV) | Size (nm) | PI | Z-potential (mV) |
| 12:12 | 143 ± 15 | 0.4 | +18 ± 3 | 105 ± 25 | 0.2 | +19 ± 2 |
| 60:12 | 232 ± 148 | 0.314 | +11 ± 1 | 221 ± 26 | 0.2 | +13 ± 2 |

Example 2.9

Nanocapsules of protamine consisting of an oily α tocopherol core and TPGS were prepared according to the one-step solvent diffusion method:

i) an aqueous solution (10 ml) in which protamine is dissolved at a concentration of 0.05 mg/ml was prepared.
ii) an oily phase made up of an ethanol/acetone solution (0.25:4.5 ml), 60 mg of α tocopherol and 24 mg of TPGS was prepared.
iii) the solutions resulting from steps i) and ii) were mixed under magnetic stirring for 10 minutes, the nanocapsules being produced spontaneously.
iv) the organic solvents were evaporated to a constant volume.

Once prepared, their mean diameter, polydispersion index (PI) as well as their surface electric charge (zeta-potential) were measured. Table 11 shows the values obtained.

TABLE 11

| Formulation | Size (nm) | PI | Z-potential (mV) |
|---|---|---|---|
| NC Pr | 189 ± 5 | 0.2 | +21 ± 6 |

Example 2.10

Nanocapsules of protamine consisting of an oily Miglyol® core were prepared according to the one-step solvent diffusion method:

i) an aqueous solution (10 ml) in which Pr is dissolved at a concentration of 0.05 w/v was prepared.

ii) an oily phase made up of an ethanol/acetone solution (0.25:4.5 ml), 62.5 µl of Miglyol® and 40 mg of sodium cholate was prepared.

iii) the solutions resulting from steps i) and ii) were mixed under magnetic stirring for 10 minutes, the nanocapsules being produced spontaneously.

iv) the organic solvents were evaporated to a constant volume.

Once prepared, their mean diameter, polydispersion index (PI) as well as their surface electric charge (zeta-potential) were measured. Table 12 shows the values obtained for the mentioned parameters.

TABLE 12

| Formulation | Size (nm) | PI | Z-potential (mv) |
|---|---|---|---|
| NC Pr | 551 ± 50 | 0.6 | +47 ± 1 |

Example 2.11

Nanocapsules of protamine consisting of an oily Miglyol® core were prepared according to the two-step solvent diffusion method:

i) an oily phase made up of an ethanol/acetone solution (0.25:4.5 ml), 62.5 µl of Miglyol® and 40 mg of sodium cholate was prepared.

ii) the solution produced in step i) was added to 10 ml of an aqueous solution under magnetic stirring and kept therein for 10 minutes, the nanoemulsion is thereby produced spontaneously:

iii) the organic solvents were evaporated to a constant volume.

iv) the nanoemulsion produced in step iii) was coated by means of an incubation process with an aqueous solution (1 ml) made up of Pr at a concentration of 1 or 2 mg/ml, in a proportion of 1:1 and 1:2 (ml of nanoemulsion:mg of protamine), the coating being produced immediately regardless of the temperature.

Once prepared, their mean diameter, polydispersion index (PI) as well as their surface electric charge (zeta-potential) were measured. Table 13 shows the values obtained for the mentioned parameters according to the amount of Pr in step iv).

TABLE 13

| Formulation | Size (nm) | PI | Z-potential (mv) |
|---|---|---|---|
| NC Pr (1 ml of NE per 1 mg of peptide) | 590 ± 7 | 0.270 | +43 ± 1 |

Example 2.12

Nanocapsules of protamine consisting of an oily α tocopherol core were prepared according to the one-step sonication method:

i) an oily phase made up of a solution of 24 mg of PEG-stearate, 120 mg of α tocopherol in dichloromethane (1 ml) was prepared.

ii) an aqueous solution in which protamine is dissolved at a concentration of 0.05 w/v was prepared.

iii) the solution produced in step i) was added to 2 ml of water and was sonicated for 30 seconds.

iv) the produced emulsion was diluted with the solution produced in ii) (1:10 dilution); to form the NC.

v) the organic solvents were evaporated to a constant volume.

Once prepared, their mean diameter, polydispersion index as well as their surface electric charge (zeta-potential) were measured. Table 14 shows the values obtained.

TABLE 14

| Formulation | Size (nm) | PI | Z-potential (mv) |
|---|---|---|---|
| NC Protamine | 340 ± 131 | 0.4 | −5 ± 1 |

Example 2.13

Nanocapsules of protamine consisting of an oily α tocopherol core were prepared according to the one-step homogenization method:

i) an oily phase made up of a solution of 24 mg of PEG-stearate, 120 mg of α tocopherol in dichloromethane (1 ml) was prepared.

ii) an aqueous solution in which protamine is dissolved at a concentration of 0.05 w/v was prepared.

iii) the solution produced in step i) was added to 2 ml of water and homogenized at 16,000 rpm for 5 minutes and then at 19,000 rpm for another 5 minutes.

iv) the produced emulsion was diluted with the solution prepared in ii) (1:10 dilution) and homogenized for 3 minutes at 22,000 rpm; to form the NC.

v) the organic solvents were evaporated to a constant volume.

Once prepared, their mean diameter, polydispersion index as well as their surface electric charge (zeta-potential) were measured. Table 15 shows the values obtained for the mentioned parameters.

TABLE 15

| Formulation | Size (nm) | PI | Z-potential (mv) |
|---|---|---|---|
| NC Pr | 289 ± 190 | 0.3 | +1 ± 2 |

Example 2.14

Nanocapsules of protamine consisting of an oily α tocopherol core were prepared according to the two-step sonication method:
i) an oily phase made up of a solution of 24 mg of PEG-stearate, 120 mg of α tocopherol in dichloromethane (1 ml) was prepared.
ii) the solution produced in step i) was added to 2 ml of water and was sonicated for 30 seconds.
iii) the produced emulsion was diluted with water (1:10 dilution).
iv) the organic solvents were evaporated to a constant volume to form a cationic nanoemulsion.
v) the nanoemulsion produced in step iv) was coated by means of an incubation process with an aqueous solution (1 ml) made up of Pr at a concentration of 1 or 2 mg/ml, in a proportion of 1:1 and 1:2 (ml of nanoemulsion:mg of protamine), the coating being produced immediately regardless of the temperature.

Once prepared, their mean diameter, polydispersion index as well as their surface electric charge (zeta-potential) were measured. Table 16 shows the values obtained.

TABLE 16

| Formulation | Size (nm) | PI | Z-potential (mv) |
|---|---|---|---|
| Nanoemulsion | 201 ± 70 | 0.3 | −16 ± 5 |
| NC Pr Incubation (1 ml of NE/mg of Pr) | 160 ± 15 | 0.2 | −4 ± 1 |
| NC Pr Incubation (0.5 ml of NE/mg of Pr) | 151 ± 13 | 0.1 | −4 ± 1 |

Example 2.15

Nanocapsules of protamine consisting of an oily α tocopherol core were prepared according to the two-step homogenization method:
i) an oily phase made up of a solution of 24 mg of PEG-stearate, 120 mg of α tocopherol in dichloromethane (1 ml) was prepared.
ii) the solution produced in step i) was added to 2 ml of water and homogenized at 16,000 rpm for 5 minutes and then at 19,000 rpm for another 5 minutes.
iii) the produced emulsion was diluted with water (1:10 dilution) and homogenized for 3 minutes at 22,000 rpm.
iv) the organic solvents were evaporated to a constant volume to form a nanoemulsion.
v) the nanoemulsion produced in step iv) was coated by means of an incubation process with an aqueous solution (1 ml) made up of protamine at a concentration of 1 or 2 mg/ml, in a proportion of 1:1 and 1:2 (ml of nanoemulsion:mg of protamine), the coating being produced immediately regardless of the temperature.

Once prepared, their mean diameter, polydispersion index as well as their surface electric charge (zeta-potential) were measured. Table 17 shows the values obtained for the mentioned parameters.

TABLE 17

| Formulation | Size (nm) | PI | Z-potential (mv) |
|---|---|---|---|
| Nanoemulsion | 187 ± 36 | 0.3 | −11 ± 4 |
| NC Pr Incubation (1 ml of NE/mg of Pr) | 165 ± 43 | 0.1 | −1 ± 1 |
| NC Pr Incubation (0.5 ml of NE/mg of Pr) | 170 ± 37 | 0.2 | −4 ± 7 |

Example 3

Evaluation of the Physicochemical Characteristics of the Nanocapsules of Protamine with Oily α Tocopherol Core According to the Amount of Protamine Example 3.1

Nanocapsules of protamine consisting of an oily α tocopherol core were prepared according to the one-step solvent diffusion method:
i) an aqueous protamine solution (10 ml) in which 1 to 100 mg of protamine are dissolved was prepared.
ii) an oily phase made up of an ethanol/acetone solution (0.25:4.5 ml), 60 mg of α tocopherol, 5 mg of sodium cholate and 12 mg of PEG-stearate was prepared.
iii) the solution produced in step ii) was added to 10 ml of the aqueous protamine solution prepared in i) under magnetic stirring and kept therein for 10 minutes, the nanocapsules are thereby produced spontaneously.
iv) the organic solvents were evaporated to a constant volume.

Once prepared, their mean diameter, polydispersion index (PI) as well as their surface electric charge (zeta-potential) were measured. Table 18 shows the values obtained for the mentioned parameters according to the amount of protamine in the aqueous solution of step i). The possibility of producing the system despite Pr variation can be observed.

TABLE 18

| Formulation | Protamine step i (mg) | Size (nm) | PI | Z-potential (mv) |
|---|---|---|---|---|
| NC Pr | 100 | 196 ± 10 | 0.2 | +7 ± 6 |
| NC Pr | 50 | 228 ± 28 | 0.2 | +4 ± 6 |
| NC Pr | 25 | 203 ± 10 | 0.2 | +10 ± 2 |
| NC Pr | 10 | 207 ± 9 | 0.2 | +15 ± 8 |
| NC Pr | 5 | 214 ± 10 | 0.2 | +18 ± 4 |
| NC Pr | 1 | 213 ± 23 | 0.2 | +7 ± 22 |

Example 4

Evaluation of the Capacity to Encapsulate Lipophilic Drug Docetaxel in Nanocapsules of Protamine Nanocapsules of protamine with an oily core made up of PEG stearate and α tocopherol or Miglyol® were prepared. A lipophilic drug was then incorporated, using to that end docetaxel, a practically water insoluble anti-tumor agent. The preparation method corresponds to the method described previously in Example 2.1 with a modification since a small aliquot of a stock solution of the active ingredient in ethanol (1-100 mg/ml) is incorporated to the oily phase. The organic solvents were then eliminated by means of the rotavapor until producing a constant volume, docetaxel-encapsulating nanocapsules of protamine being formed.

Once the nanocapsules were prepared according to the method of the invention, the encapsulation efficiency was determined (evaluating the free drug by means of high-performance liquid chromatography, with λ=227 nm), an encapsulation efficiency of 35% being obtained. The mean particle diameter, polydispersion index and zeta-potential parameters were also measured (Table 19). The possibility of effectively incorporating hydrophobic active substances can be seen, without there being significant differences in the inclusion of Pr in the NE.

TABLE 19

| Formulation | Size (nm) | PI | Z-potential (mV) | Encapsulation (%) |
|---|---|---|---|---|
| NE α tocopherol | 214 ± 10 | 0.1 | −24 ± 4 | |
| NE α tocopherol (10 μg/ml DCX) | 227 ± 11 | 0.2 | −12 ± 3 | 32 ± 10 |
| NC Pr/α tocopherol | 234 ± 5 | 0.2 | +17 ± 4 | |
| NC Pr/α tocopherol (10 μg/ml DCX) | 226 ± 9 | 0.2 | −2 ± 1 | 38 ± 4 |
| NC Pr/α tocopherol (20 μg/ml DCX) | 223 ± 6 | 0.2 | +4 ± 7 | 37 ± 6 |
| NE Miglyol ® | 209 ± 4 | 0.1 | −27 ± 1 | |
| NE Miglyol ® (10 μg/ml DCX) | 242 ± 17 | 0.2 | −13 ± 1 | 35 ± 17 |
| NC Pr Miglyol ® | 227 ± 6 | 0.1 | +20 ± 2 | |
| NC Pr Miglyol ® (10 μg/ml DCX) | 236 ± 12 | 0.2 | −1 ± 2 | 30 ± 12 |
| NC Pr Miglyol ® (20 μg/ml DCX) | 233 ± 6 | 0.2 | 4 ± 7 | 30 ± 10 |

Example 5

Study of the Cell Proliferation Inhibition Capacity of the Nanocapsules of Protamine The nanocapsules of protamine were prepared according to the method described in Example 4 for the purpose of evaluating the potential of docetaxel-encapsulating nanocapsules of protamine to inhibit cell proliferation of lung cancer cell lines NCL-H460 and A549 and pancreatic cancer cell lines MiaPaCa2 and BxPC3. Four treatments are analyzed for this study; (i) ethanol (ii) DCX solution in ethanol, (iii) blank nanocapsules as controls and (iv) nanocapsules loaded with DCX, diluted in culture medium (DMEM). After the incubation time (24 and 48 h), the samples were treated with crystal violet and the solubilized cells were quantified by spectrophotometric determination (λ=590 nm). The following drawings (FIGS. 1-4) show the results of this study:

As can be observed in the different graphs, the activity of docetaxel in ethanol is comparable with that of the same drug encapsulated in the NCs of Pr, for different times and different cell lines. This would allow concluding the possibility of administering these systems in vivo without the need of other excipients, such as Cremophor or high Tween 80 concentrations, causing the irrational biodistribution of these systems and the main adverse reactions that they have.

Example 6

Evaluation of the Capacity to Encapsulate Other Lipophilic Molecules in the Nanocapsules of Protamine Example 6.1

Encapsulation of Rhodamine 6G in the Nanocapsules of Protamine

Nanocapsules of protamine with an oily core made up of α tocopherol were prepared. A lipophilic molecule was then incorporated, using to that end rhodamine 6G, an organic heterocyclic compound, in addition to being a fluorescent contrast medium and belonging to the family of rhodamines. The preparation method corresponds to the method described previously in Example 2.1 with a modification since a small aliquot of a stock solution of the active ingredient in ethanol (1 mg/ml) is incorporated to the oily phase. The organic solvents of the system were then eliminated until producing a constant volume, the rhodamine 6G-encapsulating nanocapsules of protamine being formed.

Once the nanocapsules were prepared according to the method of the invention, the encapsulation efficiency was determined (evaluating the amount of free rhodamine by means of visible spectroscopy, λ=530 nm). The mean particle diameter, polydispersion index and zeta-potential parameters are shown in Table 20. As can be concluded, it is possible to include different hydrophobic molecules in the core of the NCs of Pr.

TABLE 20

| Formulation | Size (nm) | PI | Z-potential (mv) | Encapsulation % |
|---|---|---|---|---|
| NC Protamine 1% rhodamine | 230 ± 4 | 0.2 | +24 ± 2 | 58 ± 1 |

Example 6.2

Encapsulation of Curcumin in the Nanocapsules of Protamine

Nanocapsules of protamine with an oily core made up of α tocopherol were prepared. A lipophilic molecule was then incorporated, using to that end curcumin, a natural phenol with certain anti-tumor, analgesic and antimicrobial activity, among others. The preparation method corresponds to the method described previously in Example 2.8, using Tween 80 as surface active agent, in an α tocopherol:Tween 80 mass ratio of 60:12; and with a modification, since a small aliquot of a stock solution of the active ingredient in ethanol (1 mg/ml) is incorporated to the oily phase. The organic solvents of the system were then eliminated until producing a constant volume, curcumin-encapsulating nanocapsules of protamine being formed.

Once the nanocapsules were prepared according to the method of the invention, the encapsulation efficiency was determined (evaluating the amount of free curcumin by means of fluorescence).

The mean particle diameter, polydispersion index and zeta-potential parameters are shown in Table 21. As can be concluded, it is possible to include different hydrophobic molecules in the core of the NCs of Pr, regardless of the surfactant used.

TABLE 21

| | Theoretical curcumin (%) | Size (nm) | PI | Z-potential (mv) | Encapsulation (%) |
|---|---|---|---|---|---|
| NC | 10 | 198 ± 31 | 0.2 | +33 ± 15 | 73 ± 14 |
| Protamine | 30 | 188 ± 27 | 0.2 | +18 ± 9 | 65 ± 8 |

Example 7

Evaluation of the Recombinant Hepatitis B Antigen Adsorption Capacity in Nanocapsules of Protamine Nanocapsules of protamine with an oily core made up of PEG stearate were prepared using α tocopherol, squalene or Miglyol® 812 as oil. A hydrophilic antigen was then associated, using to that end the recombinant hepatitis B antigen (rHBsAg). The preparation method corresponds to the method described previously in Example 2.1. An aliquot of the antigen was then incubated with the already formed nanocapsules of protamine, taking to that end different mass ratios (protamine:antigen).

Once the nanocapsules with the adsorbed antigen were prepared, the association efficiency of some of these formulations was determined through ELISA and the mean particle diameter, polydispersion index and zeta-potential parameters were quantified (Table 22). As can be observed in the table, the NCs of Pr effectively associate a large amount of rHBsAg to their surface.

TABLE 22

| Formulation | Size (nm) | PI | Z-potential (mV) | Association (%) |
|---|---|---|---|---|
| NC Pr Miglyol ®:rHbAg 6:1 | 218 ± 15 | 0.2 | +18 ± 3 | |
| NC Pr Miglyol ®:rHbAg 4:1 | 211 ± 18 | 0.2 | +17 ± 3 | 70 ± 1 |
| NC Pr Miglyol ®:rHbAg 2:1 | 222 ± 27 | 0.2 | +5 ± 9 | |
| NC Pr Miglyol ®:rHbAg 1:1 | 263 ± 76 | 0.3 | −1 ± 1 | |
| NC Pr α tocopherol:rHbAg 6:1 | 221 ± 19 | 0.1 | +17 ± 7 | 82 ± 4 |
| NC Pr α tocopherol:rHbAg 4:1 | 226 ± 11 | 0.1 | +23 ± 1 | 72 ± 5 |
| NC Pr α tocopherol:rHbAg 2:1 | 206 ± 19 | 0.2 | +6 ± 10 | |
| NC Pr α tocopherol:rHbAg 1:1 | 209 ± 10 | 0.2 | +12 ± 9 | |
| NC Pr α squalene:rHbAg 4:1 | 226 ± 19 | 0.2 | +8 ± 3 | 82 ± 1 |

Example 8

Immunization Study with the Nanocapsules of Protamine Loaded with Recombinant Hepatitis B Antigen Nanocapsules of protamine with an oily α tocopherol (TCPH) and squalene (SQL) core were prepared. Recombinant hepatitis B antigen (rHBsAg) was then associated at an NC:HBsAg ratio of 4:1. The preparation method corresponds to the method described previously in Example 7.

The ability of NCs to induce immune response was measured in female BALB/c mice, the response was quantified through ELISA on days 42, 126 and 183. The animals experienced 12 hours of light and 12 hours of dark cycles with a constant temperature at 22° C., with water and food ad libitum. The animals were conscious during immunization and sampling. The mice were used according to the guidelines of the Spanish legislation (Royal Decree 1201/2005). Groups of 7 mice were randomly chosen and immunized with a dose of 10 μg of antigen adsorbed in the NCs Pr on days 0 and 28 for intramuscular administration (im) and days 0, 28 and 112 through intranasal route (in). A combined administration was tested for NC Pr-TOCOPH, the administration on day 0 being intramuscular and the administration of days 28 and 112 being intranasal (im, in). The following graph shows the results obtained for the conducted study.

Figure 5:
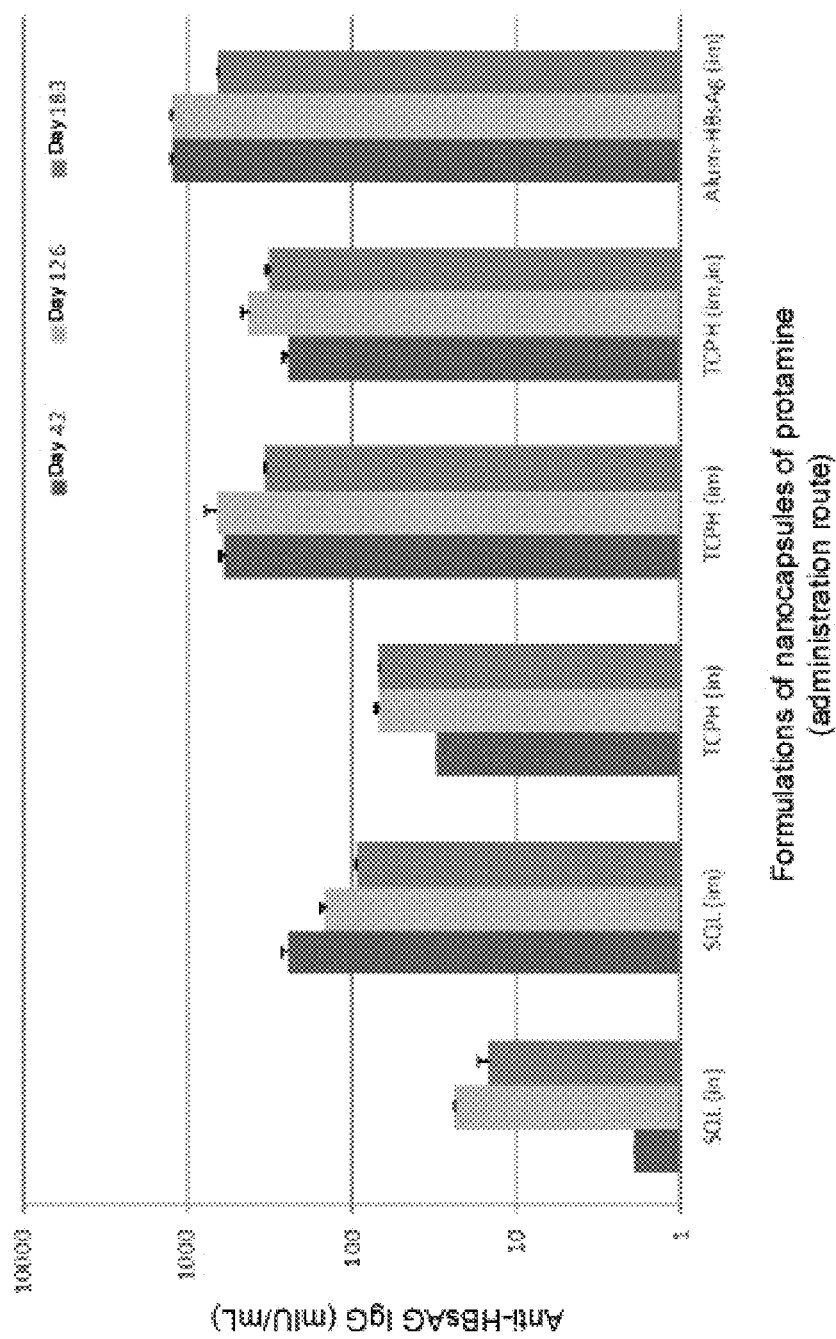
FIG. 5: Blood IgG antibody levels in mice after the administration of nanocapsules of protamine with squalene oil (SQL) and α tocopherol (TCPH) loaded with the hepatitis B antigen (10 µg) by nasal administration (in) (3 doses), intramuscular administration (im) (2 doses), and a combined schedule (im, in) (1 intramuscular dose and 2 nasal doses); compared with the antigen adsorbed in aluminum hydroxide administered by intramuscular administration (2 doses).

Taking into account that the value of 100 (mIU/ml) IgG is considered protective values, it can be seen in FIG. 5 that the NCs Pr reach said protection by intramuscular administration (im) and combined treatment (im, in) regardless of the oil used. Although this level is not achieved by nasal administration, it is known that a transmucosal administration such as this preferably stimulates a cell-type immune response; so the protection for this disease is not ruled out.

Example 9

Evaluation of the Influenza Antigen Adsorption Capacity to the Nanocapsules of Protamine with α Tocopherol Core Nanocapsules of protamine with an oily core made up of PEG stearate were prepared using α tocopherol as oil. A hydrophilic protein antigen was then associated, using to that end the H1N1 influenza antigen (HI). The preparation method corresponds to the method described previously in Example 2.1. An aliquot of the antigen was then incubated with the already formed nanocapsules of protamine, taking to that end different mass ratios (protamine:antigen).

Once the nanocapsules with the adsorbed antigen were prepared, the association efficiency of the 4:1 NC:antigen formulation was determined through Western Blot and the mean particle diameter, polydispersion index and zeta-potential parameters were evaluated (Table 20).

As can be seen in Table 23, the physicochemical characteristics of the system are not affected after the adsorption of HI. The NCs Pr efficiently associate the protein antigen.

TABLE 23

| Formulation | Size (nm) | PI | Z-potential (mV) | % Association |
|---|---|---|---|---|
| NC Pr α tocopherol | 211 ± 9 | 0.2 | +17.42 ± 4 | |
| NC Pr α tocopherol:HI 6:1 | 207 ± 10 | 0.1 | +20 ± 7 | |
| NC Pr α tocopherol:HI 4:1 | 205 ± 10 | 0.1 | +13 ± 3 | 71 ± 10 |
| NC Pr α tocopherol:HI 2:1 | 321 ± 184 | 0.1 | +12 ± 3 | |

Example 10

Immunization Study with the Nanocapsules of Protamine Loaded with H1N1 Influenza Antigen Nanocapsules of protamine with an oily α tocopherol core were prepared. HI antigen was then associated at an NC:HI ratio of 4:1. The preparation method corresponds to the method described previously in Example 9.

Figure 6:
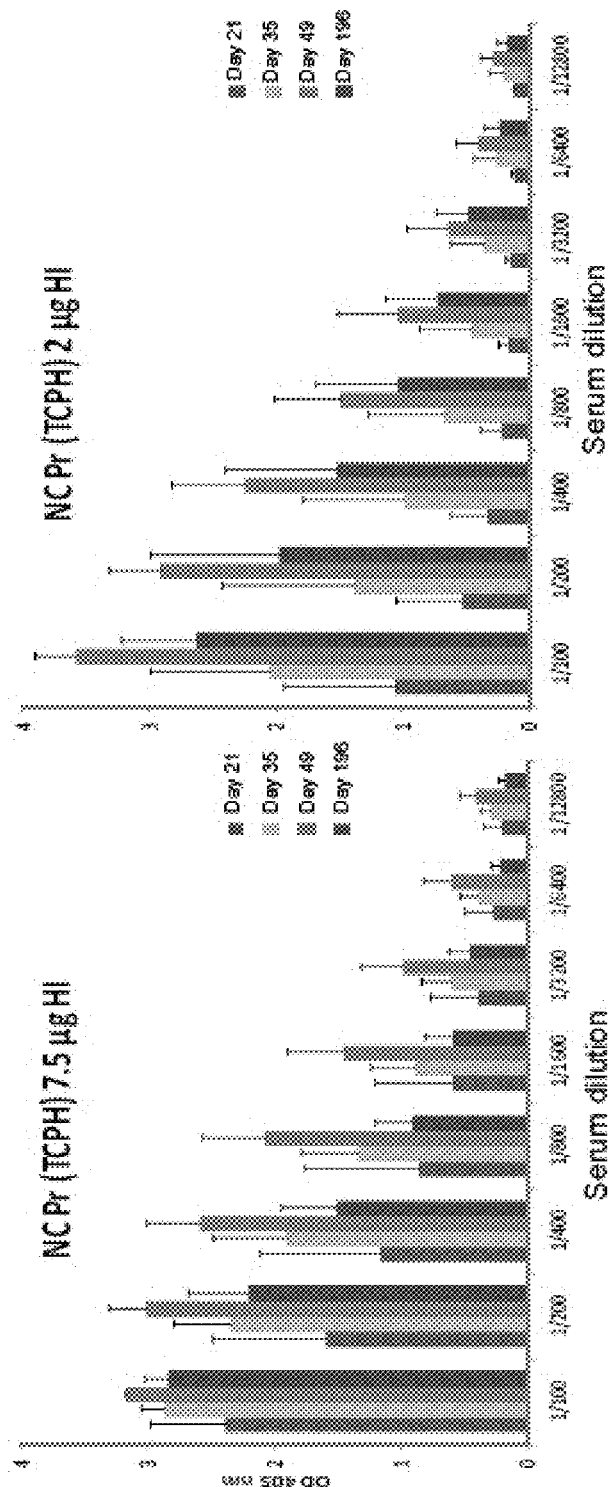
FIG. 6: Levels of absorbance produced by the blood IgG antibodies in mice after the administration of nanocapsules of protamine with an α tocopherol (TCPH) core loaded with the influenza antigen in doses of 2 and 7.5 µg, by subcutaneous administration.
Figure 7:
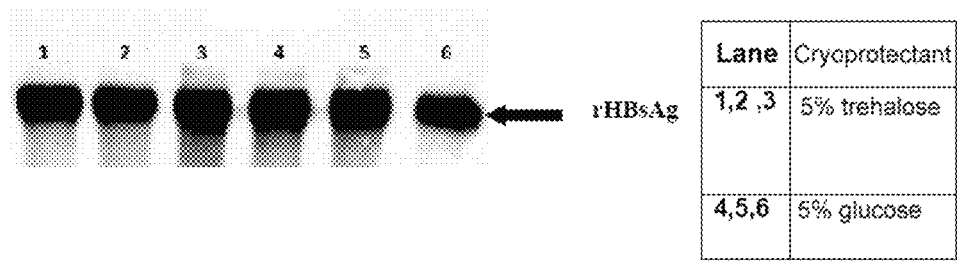
FIG. 7: Western blot of recombinant hepatitis B antigen adsorbed in the nanocapsules of protamine after the lyophilization process.
Figure 8:
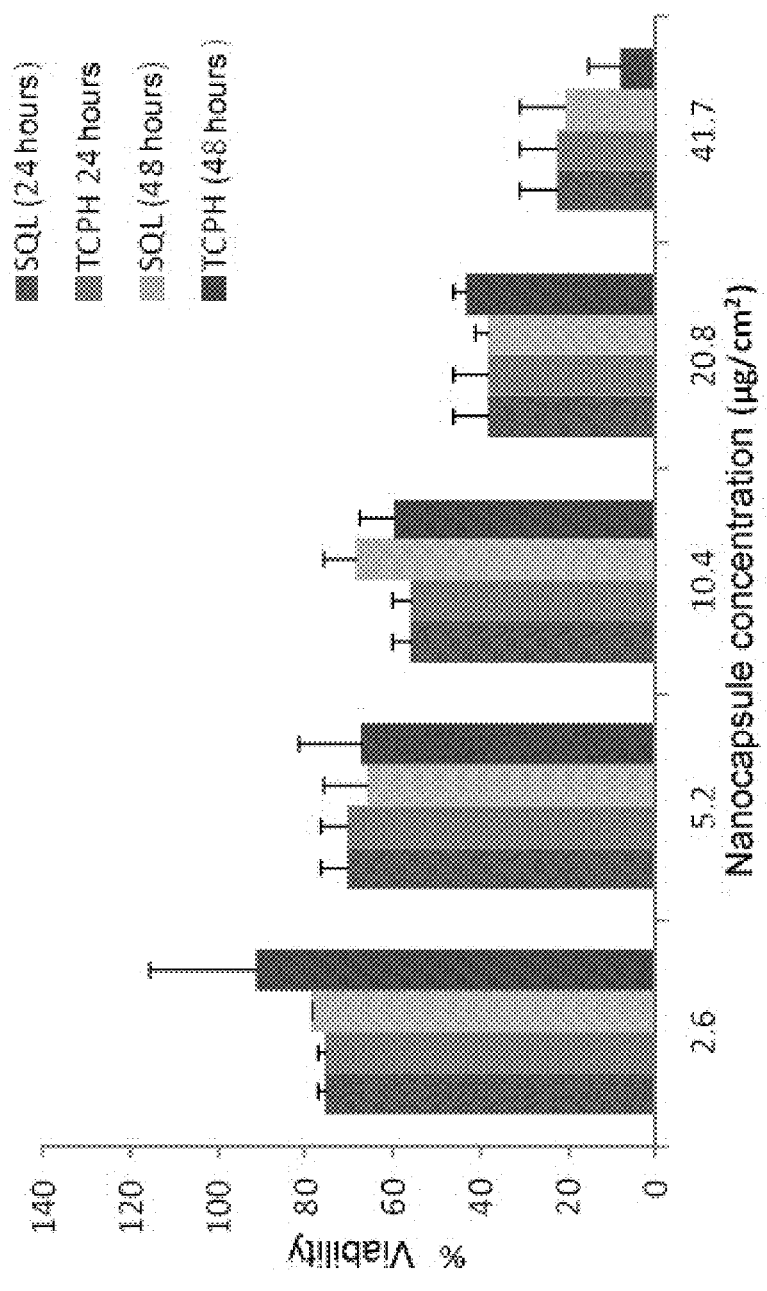
FIG. 8: Viability of the RAW 264.7 macrophage cell line after 24 and 48 hours of contact with nanocapsules of protamine and squalene (SQL) or α tocopherol (TCPH) core.
Figure 9:
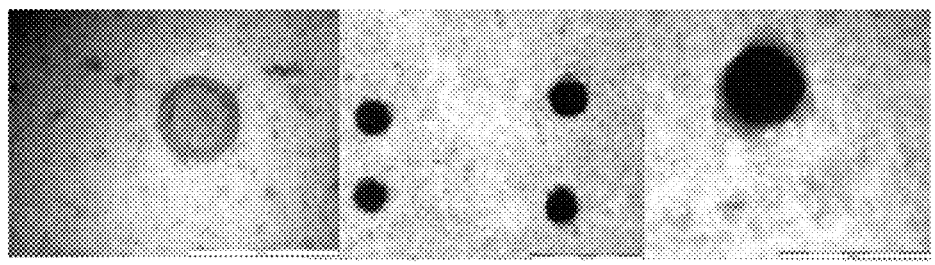
FIG. 9: Transmission electron microscopy (TEM) images of nanocapsules of protamine prepared with the combination of PEG stearate/sodium cholate surfactants and Miglyol® oil.
Figure 10:
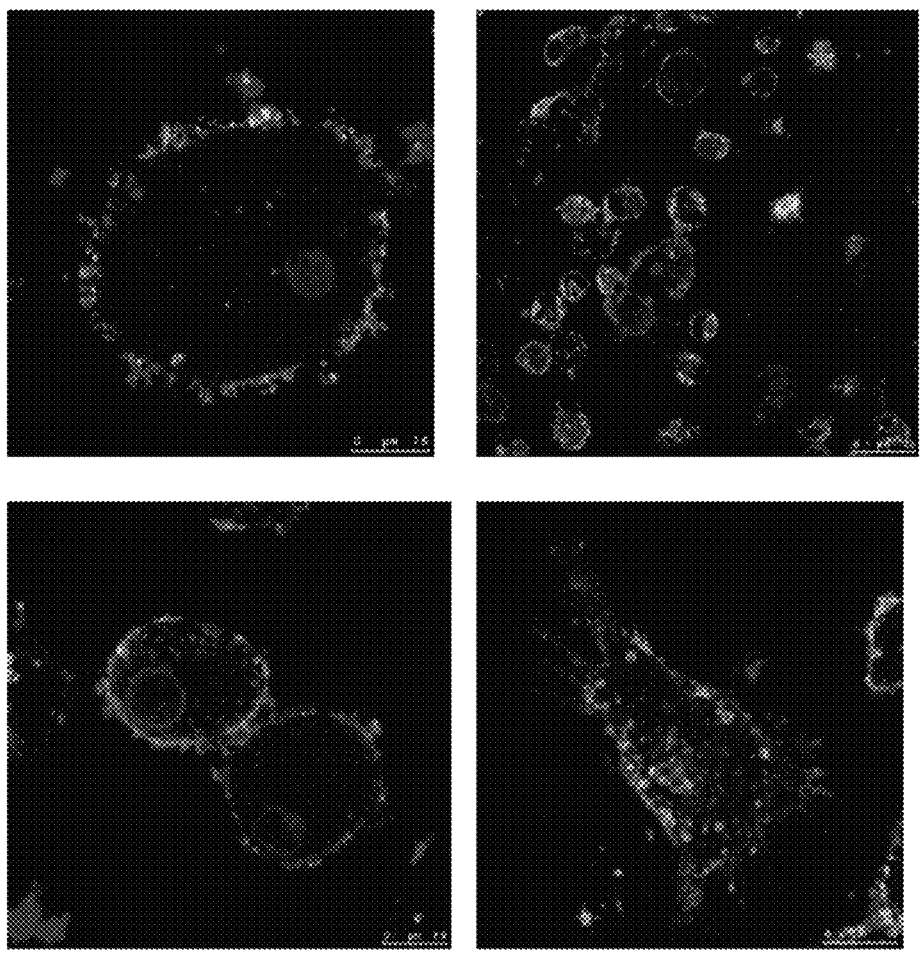
FIG. 10: Confocal microscopy images of nanocapsules of protamine prepared with the PEG stearate/sodium cholate surfactant and α tocopherol oil. As an active molecule, they are loaded with the influenza (H1N1) antigen.

The ability of NCs to induce immune response was measured in female BALB/c mice, the response was quantified through ELISA on days 21, 35, 49 and 196. The animals experienced 12 hours of light and 12 hours of dark cycles with a constant temperature at 22° C., with water and food ad libitum. The animals were conscious during immunization and sampling. The mice were used according to the guidelines of the Spanish legislation (Royal Decree 1201/2005). Groups of 5 mice were randomly chosen and subcutaneously immunized with a dose of 7.5 or 2 μg of antigen adsorbed in the nanocapsules of Pr on days 0, 21, 35 and the presence of IgG antibodies specific against the antigen was evaluated by means of ELISA techniques. FIG. 6 shows the results obtained for the conducted study.

As can be observed in the image, the NCs Pr induce higher hemagglutination inhibition titers than a 1:64 dilution, which is considered sufficient for protection against influenza infection.

Example 11

Evaluation of the Genetic Material Adsorption Capacity to the Nanocapsules of Protamine with α Tocopherol Core Nanocapsules of protamine with an oily core made up of α tocopherol were prepared using PEG stearate or PEG stearate and sodium cholate as surfactant. The genetic material EGFP-C1 was then associated. The preparation method corresponds to the method described previously in Example 2.1. An aliquot of the plasmid was then incubated with the already formed nanocapsules of protamine, taking to that end, different loading ratios at 5, 10 and 20% with respect to the mass of Pr. Once the nanocapsules with the adsorbed pDNA were incubated, the mean particle diameter, polydispersion index and zeta-potential parameters were evaluated (Table 24).

As shown in Table 21, there is a significant decrease in the surface charge of the systems, a reversal of potential even being observed, showing that the genetic material is adsorbed to the surface of the NCs Pr.

TABLE 24

| Formulation | Surfactants | Size | PdI | Zeta |
|---|---|---|---|---|
| NC Pr α tocopherol | PEG stearate | 245 ± 11 | 0.2 | −8 ± 7 |
| NC Pr α tocopherol (5% pDNA loading) | | 262 ± 16 | 0.2 | −14 ± 6 |
| NC Pr α tocopherol (10% pDNA loading) | | 244 ± 3 | 0.2 | −20 ± 5 |
| NC Pr α tocopherol (20% pDNA loading) | | 248 ± 4 | 0.2 | −15 ± 1 |
| NC Pr α tocopherol | PEG stearate and | 246 ± 2 | 0.1 | +33 ± 1 |
| NC Pr α tocopherol (5% pDNA loading) | | 238 ± 4 | 0.1 | −25 ± 3 |

TABLE 24-continued

| Formulation | Surfactants | Size | PdI | Zeta |
|---|---|---|---|---|
| NC Pr α tocopherol (10% pDNA loading) | sodium cholate | 240 ± 8 | 0.2 | −24 ± 2 |
| NC Pr α tocopherol (20% pDNA loading) | | 276 ± 2 | 0.3 | −26 ± 1 |

Example 12

Example 12.1

Evaluation of the Effect of Trehalose and Glucose on the Particle Size of the Nanocapsules of Protamine after Lyophilization Process Nanocapsules of protamine with an oily core made up of PEG stearate and squalene were prepared according to the previously described method. The effect that cryoprotective agents glucose and trehalose have on the lyophilization process of the nanocapsules of Pr and the subsequent recovery of the particle size after resuspension was evaluated by assaying two cryoprotectant concentrations, 5 and 10% w/v. The influence of nanocapsule concentration (0.025; 0.05; 0.08; 0.1; 0.25; 0.5; 0.75; and 1% w/v) on the suspension to be lyophilized was also evaluated. As control, a suspension of NCs of Pr at a concentration of 1.54% was lyophilized without cryoprotectant. The results of the table show the particle size of the lyophilized nanocapsules of Pr after resuspension (Table 25).

As seen in Table 22, a dry formulation of NCs Pr which does not lose its physicochemical properties, even without using cryoprotectant, can be obtained. It is known that formulations in the form of dry powder have greater stability than formulations in the form of aqueous suspension, so it is expected that said formulation can be stable at room T.

TABLE 25

| | 5% glucose | | 10% glucose | | 5% trehalose | | 10% trehalose | |
|---|---|---|---|---|---|---|---|---|
| NC Conc. | Size (nm) | PI | Size (nm) | PI | Size (nm) | PI | Size (nm) | PI |
| 1.54% | 219 ± 83 | 0.3 | Formulation without cryoprotectant | | | | | |
| 1% | 317 ± 66 | 0.4 | 273 ± 51 | 0.4 | 330 ± 74 | 0.5 | 256 ± 39 | 0.4 |
| 0.75% | 300 ± 67 | 0.4 | 628 ± 501 | 0.6 | 320 ± 84 | 0.5 | 258 ± 45 | 0.3 |
| 0.50% | 310 ± 52 | 0.4 | 415 ± 373 | 0.4 | 320 ± 27 | 0.5 | 237 ± 31 | 0.3 |
| 0.25% | 305 ± 44 | 0.4 | 259 ± 40 | 0.4 | 303 ± 37 | 0.4 | 210 ± 46 | 0.3 |
| 0.10% | 244 ± 30 | 0.3 | 254 ± 22 | 0.3 | 285 ± 47 | 0.4 | 212 ± 27 | 0.3 |
| 0.08% | 251 ± 56 | 0.4 | 226 ± 11 | 0.3 | 229 ± 6 | 0.3 | 198 ± 39 | 0.2 |
| 0.05% | 268 ± 41 | 0.4 | 279 ± 57 | 0.3 | 204 ± 10 | 0.3 | 204 ± 33 | 0.2 |
| 0.025% | 243 ± 37 | 0.3 | 217 ± 14 | 0.3 | 184 ± 20 | 0.3 | 252 ± 68 | 0.3 |

Example 12.2

Evaluation of the Effect on the Particle Size of the Nanocapsules of Protamine and the Integrity of rHBsAg after Lyophilization Process Nanocapsules of protamine with an oily core made up of PEG stearate, sodium cholate and α tocopherol were prepared according to the previously described method. The effect of the particle size of NCs Pr at a concentration of 1% was evaluated using cryoprotective agents glucose and trehalose at a concentration of 5%. The results of the table show the particle size of the lyophilized nanocapsules of Pr after resuspension (Table 23). The integrity of the adsorbed antigen was analyzed through Western Blot.

As seen in Table 26, a dry formulation of NCs Pr with rHBsAg antigens adsorbed to their shell which does not lose its physicochemical properties can be obtained. The image shows the integrity of the NC-Pr-associated rHBsAg antigen after the lyophilization process.

The Western Blot image shows that there is no degradation after the lyophilization process.

TABLE 26

| Formulation | NC concentration (% w/w) | Cryoprotectant | Size | PDI |
|---|---|---|---|---|
| Non-lyophilized NC Pr | 1.64 | | 268 ± 35 | 0.2 |
| Lyophilized NC Pr | 0.5 | Trehalose | 228 ± 43 | 0.3 |
| Lyophilized NC Pr | 1 | Trehalose | 188 ± 7 | 0.3 |
| Lyophilized NC Pr | 1 | Glucose | 254 ± 109 | 0.3 |

Example 13

Evaluation of the Particle Size Variation of the Formulation of Nanocapsules of Protamine During Storage Nanocapsules of protamine with an oily core made up of α tocopherol and PEG-st were prepared according to the method described previously in Example 2.3 with 12 mg of PEG-st. Particle size measurements were taken for a long period of time in order to obtain information about system size evolution over time. The effect of storage temperature (4-8° C.) on nanocapsule stability was also evaluated. The results depicted in Table 27 show little variability of the size of the nanocapsules of Pr during storage

TABLE 27

| Time | Size |
|---|---|
| Day 0 | 261 ± 13 |
| Day 7 | 261 ± 7 |
| Day 14 | 263 ± 10 |
| Day 21 | 258 ± 8 |
| Day 28 | 265 ± 7 |
| 2 months | 270 ± 12 |
| 3 months | 300 ± 15 |
| 4 months | 289 ± 18 |

Example 14

Evaluation of the Cell Viability of the Nanocapsules of Protamine

For the purpose of evaluating the viability of the nanocapsules of protamine in RAW 264.7 immune cells. To that end, nanocapsules of protamine were prepared according to the method described in Example 2.1 with squalene (SQL) and α tocopherol oil (TCPH). For this study, different concentrations of nanocapsules were incubated in the mentioned cell line and their viability was quantified after 24 or 48 hours through the QCCS (Quick Cell Countig Solution) method.

As shown in FIG. 5, at different concentrations of nanocapsules of protamine the viability is at about 75% even after 48 hours of incubation, thus providing the toxicity values of the invention Example 15

Evaluation of the Capacity of the Nanocapsules of Protamine to Induce Cytokine Secretion in Peripheral Blood Mononuclear Cells Nanocapsules of protamine with an oily α tocopherol or squalene core were prepared according to the method described in Examples 2.3 and 2.5, respectively.

Once the nanocapsules were prepared, the different cytokines secreted by peripheral blood mononuclear cells were determined. To that end, blood from three healthy individuals was heparinized, diluted in PBS and separated by gradient centrifugation through Ficoll-Hypaque to enable separating the mononuclear cells. For quantifying cytokine production, $2 \times 10^5$ of these cells were incubated for 24 hours in the presence of nanocapsules of protamine with an oily α tocopherol or squalene core at two concentrations of 10 and 100 µg/ml, using LPS (10 µg/ml) as positive control. The secretion levels were determined using Th1/Th2 FlowCytomix™ following the manufacturer's indications. As shown in Table 28, the nanocapsules can induce cytokine secretion. This response can be modulated according to the concentration and/or the component of the oily core. (n/3)=number of responding subjects.

TABLE 28

| | | µg/ml | NC Pr (SQL) | NC Pr (TCPH) | LPS |
|---|---|---|---|---|---|
| Th1 cytokines | IL 12 | 10 | + (1/3) | + (1/3) | ++ (3/3) |
| | | 100 | + (1/3) | − | |
| | IFN γ | 10 | − | − | +++ (3/3) |
| | | 100 | + (1/3) | − | |
| | IL 2 | 10 | ++ (1/3) | ++ (1/3) | ++ (3/3) |
| | | 100 | ++ (1/3) | ++ (1/3) | |
| | TNF β | 10 | + (1/3) | + (1/3) | ++ (2/3) |
| | | 100 | ++ (1/3) | ++ (1/3) | |
| Th2 cytokines | IL 10 | 10 | − | − | ++ (1/3) |
| | | 100 | − | − | |
| | IL 6 | 10 | ++ (2/3) | ++ (2/3) | ++++ (3/3) |
| | | 100 | ++ (3/3) | ++ (2/3) | |
| | IL4 | 10 | ++ (1/3) | ++ (1/3) | ++ (2/3) |
| | | 100 | +++ (1/3) | +++ (1/3) | |
| | IL5 | 10 | − | − | + (1/3) |
| | | 100 | − | − | |

TABLE 28-continued

|  |  | µg/ml | NC Pr (SQL) | NC Pr (TCPH) | LPS |
|---|---|---|---|---|---|
| Other pro-inflammatory cytokines | IL 8 | 10 | +++ (3/3) | +++ (3/3) | ++++ (3/3) |
|  |  | 100 | ++++ (3/3) | ++++ (3/3) |  |
|  | IL 1 β | 10 | +++ (1/3) | +++ (1/3) | +++ (3/3) |
|  |  | 100 | +++ (3/3) | +++ (3/3) |  |
|  | TNF α | 10 | ++ (1/3) | ++ (1/3) | ++++ (3/3) |
|  |  | 100 | ++ (1/3) | ++ (1/3) |  |

Example 16

Evaluation of Complement Cascade Activation by the Nanocapsules of Protamine

Nanocapsules of protamine with an oily α tocopherol or squalene core were prepared according to the method described in Examples 2.3 and 2.5, respectively.

Figure 11:
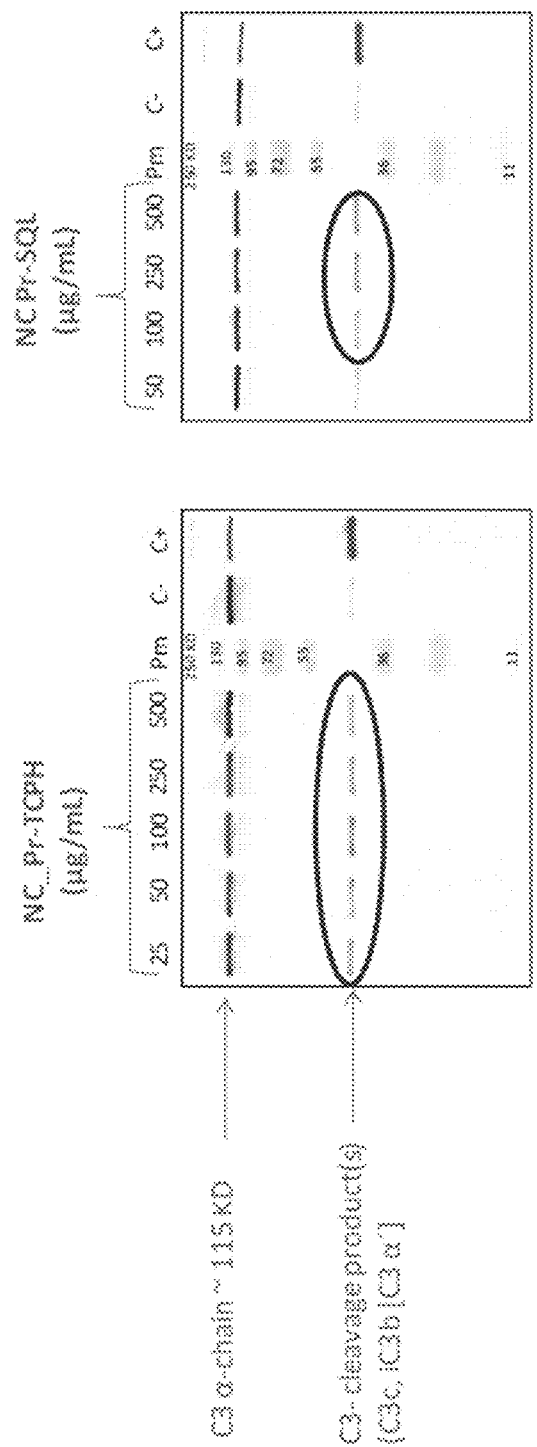
FIG. 11: Activation of the complement induced by the nanocapsules of protamine, analyzed through Western blot. Different concentrations of nanocapsules of protamine with α tocopherol (left) or squalene (right) were studied. The negative control was PBS (C−) and the positive control was cobra venom (C+).

Once the nanocapsules were prepared, complement activation was determined analyzing the C3 product through Western blot for that purpose. Different concentrations of nanocapsules of protamine were incubated with human plasma, and cobra venom was used as positive control and PBS as negative control. As shown in FIG. 11, it can be observed that the nanocapsules of protamine activate the complement cascade, depending on their oily core composition and concentration, this being a characteristic which can be used for developing new prophylactic or therapeutic immunization adjuvants.

Example 17

Evaluation of the Cell Viability in Raw 267.4 Cells after Incubation with the Nanocapsules of Protamine Nanocapsules of protamine with an oily α tocopherol core were prepared according to the method described in Example 2.3.

Once the nanocapsules were prepared, the influence of the nanocapsules of protamine on cell viability was determined with a method other than that described in Example 14.

To that end, the cell viability was measured through xCELLigence® in RAW 264.7 macrophages following the manufacturer's instructions. Three concentrations of nanocapsules were tested and cells without nanocapsules (red line) were used as positive control. The cell viability is correlated to the electrical impedance of the gold electrodes quantifying the number of cells and the morphology every 15 minutes for 48 hours.

Figure 12:
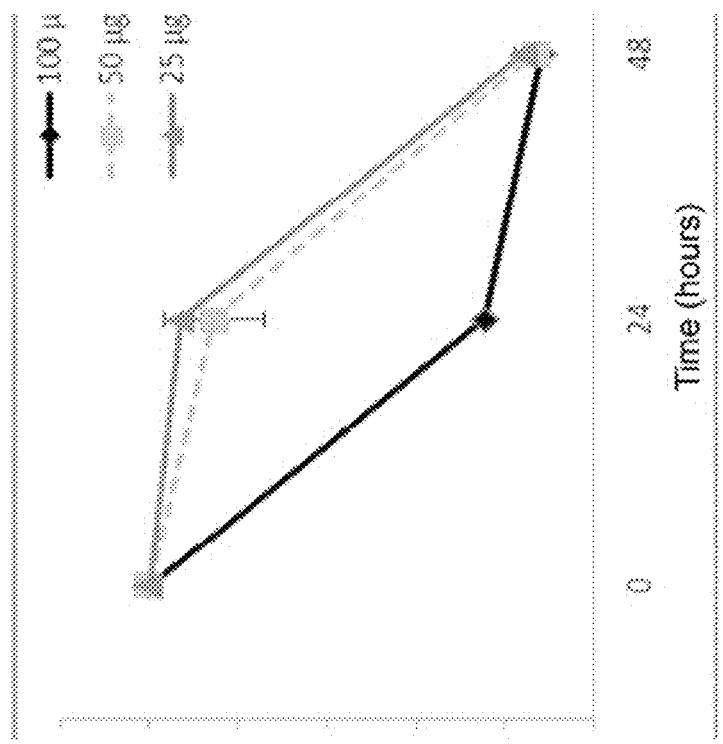
FIG. 12: Effect of the nanocapsules of protamine with an oily α tocopherol core on the viability of RAW 264.7, determined by xCELLigence. Different concentrations of nanocapsules of protamine (25 in gray, 50 in dashed line and 100 in solid black, μg/ml) were incubated. The values represent the normalized cell index with respect to the control (cells incubated only with medium).

As seen in FIG. 12, after 24 hours of continuous contact with the cells, the nanocapsules do not alter cell growth up to a concentration of 50 □g/ml (i.e. profile identical to the control).

Example 18

Evaluation of the Stability of the Lyophilized Nanocapsules of Protamine Associating Hepatitis B Antigen Nanocapsules of protamine with an oily α tocopherol core were prepared according to the method described in Example 2.3.

Once the nanocapsules were prepared, the recombinant hepatitis B antigen (rHBsAg) was associated as specified in Example 7 at an NC:rHBsAg ratio of 4:1. This formulation was then lyophilized with 5% trehalose as specified in Example 12 at a nanocapsule concentration of 1%. The lyophilized product was stored at room temperature (25° C.) and resuspended at different times for the purpose of evaluating its physicochemical properties. The integrity of the antigen was analyzed through Western blot for each time point.

Figure 13:
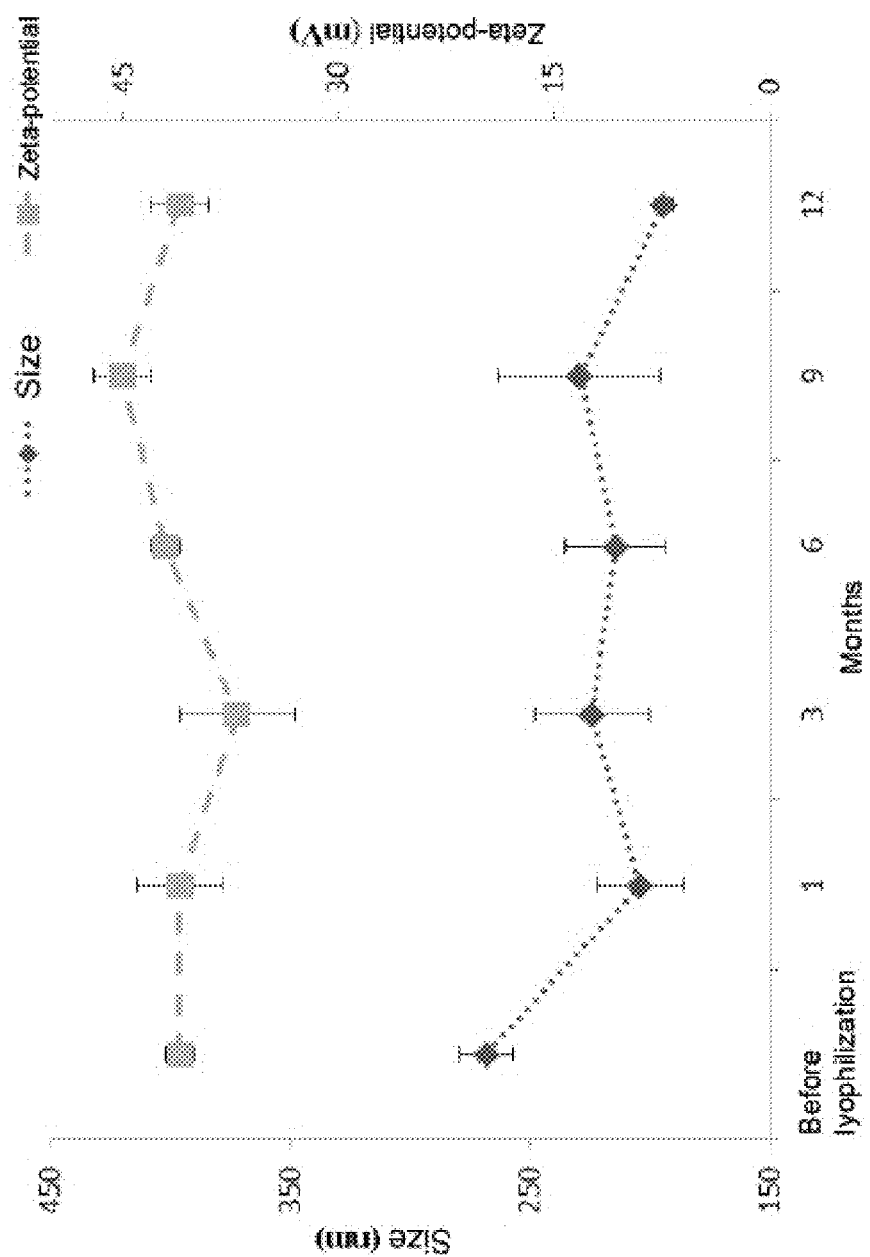
FIG. 13: Physicochemical characterization of nanocapsules of protamine loaded with lyophilized rHBsAg and resuspended; conserved at room temperature.
Figure 14:
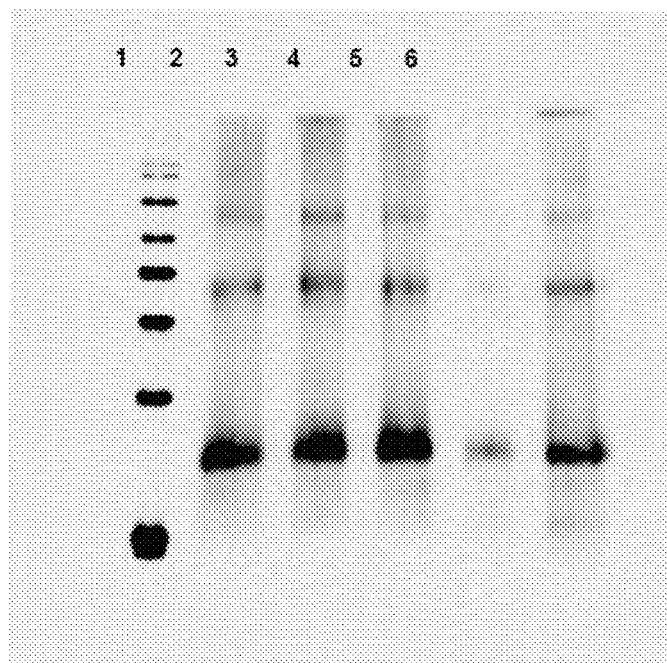
FIG. 14: Western blot analysis of the antigen (rHBsAg) associated with the nanocapsules lyophilized and conserved at room temperature for one year.

As can be observed in the physicochemical characterization of FIG. 13; the lyophilized product remains stable, with nanometric size and positive zeta-potential for at least 12 months. The Western Blot image (FIG. 14) indicates that the antigen adsorbed in the nanocapsules of protamine (lane 2, 3 and 4) does not lose its structure or antigenicity in the lyophilization process or throughout the storage time at room temperature and is comparable with the antigen that has been stored at 4° C. (lane 6). Lane 5 shows the free lyophilized rHBsAg stored at room temperature, where the relative loss of antigen compared to that associated with the nanocapsules of protamine can be seen.

The heat stability of the nanocapsules of the invention of at least one year and the protection exerted by this vehicle on the associated antigen or molecule are demonstrated with this example.

Example 19

Nanocapsules of protamine consisting of an oily α tocopherol core were prepared according to the method described in Example 2.8 with the variation of the solvent diffusion method (by dripping) for the purpose of reducing the size of the resulting formulation.

i) an aqueous solution (10 ml) in which protamine was dissolved at a concentration of 0.25 and 0.125 mg/ml was prepared.
ii) an oily phase made up of an ethanol/acetone solution (0.750:4.25 ml), 15 mg of α tocopherol and 6 mg of Tween® 80 was prepared.
iii) the ethanol solution resulting from ii) was added in aliquots of 0.250 ml every 20 seconds to i), the nanocapsules being produced spontaneously.
iv) the organic solvents were evaporated to a constant volume (5 ml).

Once prepared, their mean diameter and polydispersion index (PI) as well as their surface electric charge (zeta-potential) were measured. Table 29 shows the values obtained.

TABLE 29

| Formulation | Size (nm) | PI | Zeta-potential (mV) |
|---|---|---|---|
| NC Pr (0.25 mg/ml) | 108 ± 3 | 0.1 | 4 ± 5 |
| NC Pr (0.125 mg/ml) | 105 ± 4 | 0.1 | 4 ± 1 |

Example 20

Nanocapsules of protamine consisting of an oily Miglyol® core were prepared with the variation of the solvent diffusion method (by dripping) for the purpose of reducing the size of the resulting formulation.
  i) an aqueous solution (10 ml) in which protamine was dissolved at a concentration of 0.25 and 0.125 mg/ml was prepared.
  ii) an oily phase made up of an ethanol/acetone solution (0.750:4.25 ml), 15 mg of Miglyol® and 6 mg of Tween® 80 was prepared.
  iii) the ethanol solution resulting from ii) was added in aliquots of 0.250 ml every 20 seconds to i), the nanocapsules being produced spontaneously.
  iv) the organic solvents were evaporated to a constant volume (5 ml).

Once prepared, their mean diameter and polydispersion index (PI) as well as their surface electric charge (zeta-potential) were measured. Table 30 shows the values obtained.

TABLE 30

| Formulation | Size (nm) | PI | Zeta-potential (mV) |
|---|---|---|---|
| NC Pr (0.25 mg/ml) | 133 ± 3 | 0.2 | +1 ± 1 |
| NC Pr (0.125 mg/ml) | 141 ± 9 | 0.2 | +12 ± 14 |

Example 21

Evaluation of the Genetic Material Adsorption Capacity to the Nanocapsules of Protamine with α Tocopherol Core Nanocapsules of protamine with an oily core made up of α tocopherol were prepared taking Tween® 80 as surfactant. Genetic materials i) EGFP-C1 pDNA and ii) GL3 siRNA were then associated. The preparation method corresponds to the method described previously in Example 2.1. An aliquot of plasmid and/or siRNA (0.050 ml) was then incubated with the already formed nanocapsules of protamine, taking to that end a genetic material load of 15.4% with respect to the mass of protamine. Once the nanocapsules with the genetic material were incubated, the following parameters were evaluated: mean particle diameter, polydispersion index and zeta-potential (Table 31).

As shown in Table 31, there is a significant drop in the surface charge of the systems, a reversal of potential even being observed, indicating that the genetic material is adsorbed on the surface of the NCs Pr.

TABLE 31

| Formulation | Size | PdI | Zeta | Association efficiency |
|---|---|---|---|---|
| NC Pr α tocopherol | 238 ± 13 | 0.2 | +28 ± 4 | — |
| NC Pr α tocopherol (15.4% pDNA loading) | 256 ± 26 | 0.3 | −25 ± 2 | ≥90% |
| NC Pr α tocopherol (15.4% siRNA loading) | 259 ± 7 | 0.1 | −31 ± 15 | ≥90% |

Figure 15:
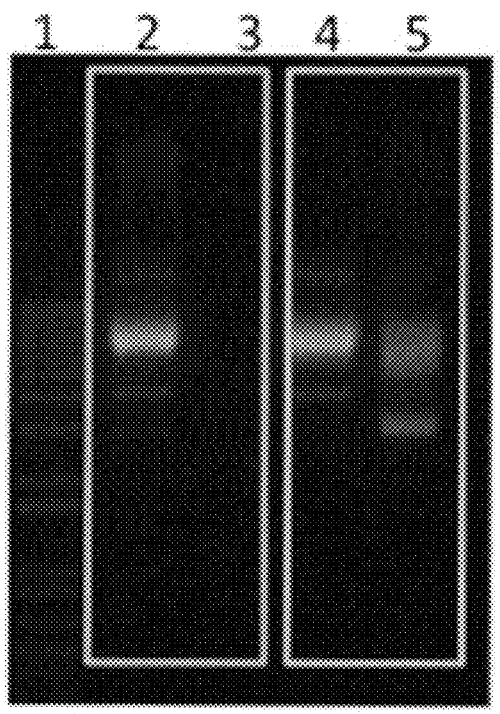
FIG. 15: Analysis of the association of pDNA with nanocapsules of protamine by means of agarose gel electrophoresis. Lanes: 1: molecular weight marker; 2: control pDNA; 3: nanocapsules of protamine+pDNA; 4: heparin+control pDNA; 5: nanocapsules of protamine+pDNA. The samples were incubated with excess heparin to allow the shift of pDNA from the formulation (2 h, 37° C.). 1 μg of pDNA per lane. Similar results were obtained for siRNA.

On the other hand, the association of the genetic material was confirmed by means of agarose gel electrophoresis (FIG. 15).

Example 22

Figure 16:
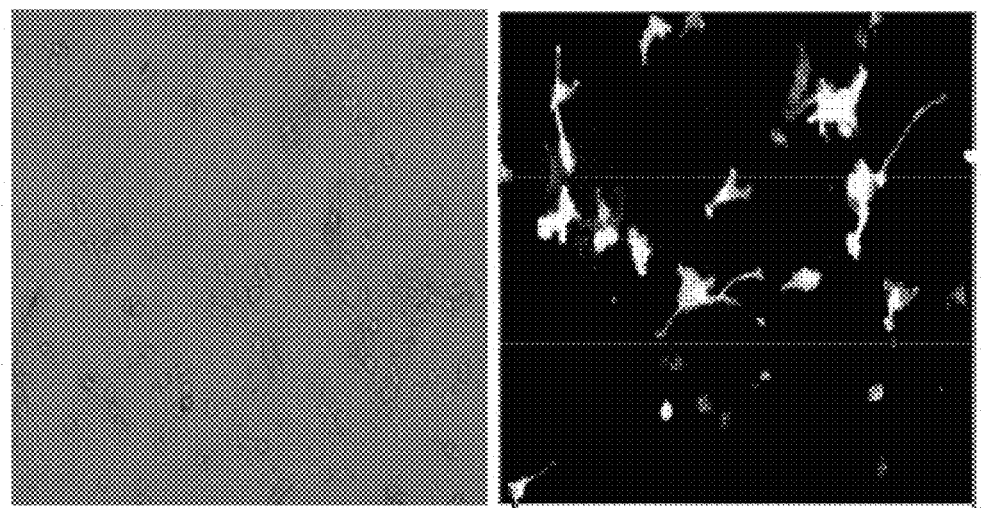
FIG. 16: Fluorescence microscopy image 48 hours post-transfection of pEGFPF associated with the nanocapsules of protamine. 1 μg pEGFPF per well (24-well plates), 4 h of incubation. Images produced 48 hours post-transfection.

Evaluation of the Capacity of the Nanocapsules of Protamine with α Tocopherol Core and Associating EGFP-C1 DNA Plasmid to be Internalized and Transfect Cancer Cells Such as the U87MG Glioblastoma Line Nanocapsules of protamine with an oily core made up of α tocopherol were prepared using Tween® 80 as surfactant. The genetic material EGFP-C1 pDNA was then associated. The preparation method corresponds to the method described previously in Example 2.1. An aliquot of plasmid (0.050 ml) was then incubated with the already formed nanocapsules of protamine (0.250 ml), taking to that end a genetic material load of 15.4% with respect to the mass of protamine. Once the nanocapsules with the adsorbed genetic material were incubated, the mean particle diameter, polydispersion index and zeta-potential parameters were evaluated (Table 31). Their efficacy in transfecting cancer cells (U87MG) was also evaluated. To that end, the systems were incubated with the cells for 4 hours and the expression of green fluorescent protein (GFP) encoded by the associated plasmid was evaluated by means of fluorescence microscopy 48 hours post-transfection as seen FIG. 16.

The invention claimed is:

1. A nanocapsule system suitable for the administration of active ingredients, comprising:
   a. a surface layer comprising the polypeptide protamine;
   b. an oily core; and
   c. a surfactant having a hydrophilic-lipophilic ratio (hydrophilic-lipophilic balance (HLB)) greater than 8, provided that said surfactant is not a phospholipid.

2. The nanocapsule system according to claim 1, wherein the surfactant is polyoxyethylene sorbitan monooleate, polyoxyethylene sorbitan monolaurate, polyoxyethylene sorbitan monostearate, polyoxyethylene sorbitan monooleate, polyoxyethylene sorbitan tristearate, polyoxyethylene sorbitan trioleate, polyoxyethylene sorbitan monolaurate, polyethylene glycol monostearate, polyethylene glycol stearate, polyethylene glycol dilaurate, polyethylene glycol monopalmitate, polyethylene glycol stearate, Poloxamer 124, Poloxamer 188, Poloxamer 237, Poloxamer 338, Poloxamer 407, polyethylene glycol-15-hydroxystearate, TPGS (D-alpha-tocopherol polyethylene glycol 1000 succinate), triethanolammonium oleate, sodium oleate, sodium cholate, sodium deoxycholate, sodium lauryl sulfate, triethanolamine oleate, tragacanth gum, and sodium dodecyl sulfate, or any combination thereof.

3. The nanocapsule system according to claim 1, wherein the surfactant is selected from the group consisting of ethoxylated sorbitan esters and fatty acid esters.

4. The nanocapsule system according to claim 3, wherein the surfactant is an ethoxylated sorbitan ester, and wherein said ethoxylated sorbitan ester is polyoxyethylene sorbitan monooleate, polyoxyethylene sorbitan monolaurate, polyoxyethylene sorbitan monostearate, polyoxyethylene sorbitan monooleate, polyoxyethylene sorbitan tristearate, polyoxyethylene sorbitan trioleate, and polyoxyethylene sorbitan monolaurate, or any combination thereof.

5. The nanocapsule system according to claim 3, wherein the surfactant is a fatty acid ester, and wherein said fatty acid ester is polyethylene glycol monostearate, polyethylene glycol stearate, polyethylene glycol dilaurate, polyethylene glycol monopalmitate, polyethylene glycol stearate, Poloxamer 124, Poloxamer 188, Poloxamer 237, Poloxamer 338, Poloxamer 407, polyethylene glycol-15-hydroxystearate, TPGS (D-alpha-tocopherol polyethylene glycol 1000 succinate), or any combination thereof.

6. The nanocapsule system according to claim 2, wherein the surfactant is triethanolammonium oleate, sodium oleate, sodium cholate, sodium deoxycholate, sodium lauryl sulfate, triethanolamine oleate, tragacanth gum, sodium dodecyl sulfate, or any combination thereof.

7. The nanocapsule system according to claim 2, wherein the surfactant is sodium cholate, polyethylene glycol stearate, polyethylene glycol-15-hydroxystearate, TPGS (D-alpha-tocopherol polyethylene glycol 1000 succinate), polyoxyethylene sorbitan monooleate, polyoxyethylene sorbitan monolaurate, or any combination thereof.

8. The nanocapsule system according to claim 1, wherein the oily lipophilic core is peanut oil, cottonseed oil, olive oil, castor oil, soybean oil, safflower oil, palm oil, α tocopherol (vitamin E), isopropyl myristate, squalene, a mixture of decanoyl- and octanoyl glyceride, oleoyl polyoxyl-6 glyceride, propylene glycol dicaprylocaprate, glycerol monooleate, glycerol monoolinoleate, or any combination thereof.

9. The nanocapsule system according to claim 8, wherein the oily lipophilic core is a mixture of decanoyl- and octanoyl glyceride, squalene or α tocopherol.

10. The nanocapsule system according to claim 1, wherein the system further comprises a lipophilic or hydrophilic active substance.

11. The nanocapsule system according to claim 10, wherein the active substance is docetaxel, a recombinant hepatitis B antigen, an influenza (H1N1) antigen, a nucleic acid, a saccharide compound, a peptide, a protein, or any combination thereof.

12. The nanocapsule system according to claim 1, wherein the nanocapsule system is lyophilized.

13. A one-step solvent diffusion method for producing the nanocapsule system as defined in claim 1, comprising:
preparing an aqueous solution comprising protamine;
preparing a solution in an organic solvent comprising an oil and one or more surfactants having a hydrophilic-lipophilic ratio greater than 8; and
mixing the aqueous solution and the solution in an organic solvent under stirring to produce nanocapsules.

14. A two-step solvent diffusion method for producing the nanocapsule system defined in claim 1, comprising:
preparing a solution in an organic solvent comprising an oil and one or more surfactants having a hydrophilic-lipophilic ratio greater than 8;
adding the solution in an organic solvent to an aqueous phase containing a water-soluble surfactant under stirring to form a nanoemulsion; and
coating the nanoemulsion by incubating the nanoemulsion with an aqueous solution comprising protamine.

15. A two-step solvent diffusion method for producing the nanocapsule system defined in claim 1, comprising:
preparing an aqueous solution comprising protamine;
preparing a solution in an organic solvent comprising an oil and at least one surfactant having a hydrophilic-lipophilic ratio greater than 8, provided that the surfactant is not a phospholipid; and
adding the solution in an organic solvent, in aliquots, at given time intervals, to the aqueous solution or adding the aqueous solution, in aliquots, at given time intervals, to the solution in an organic solvent.

16. The nanocapsule system according to claim 10, wherein the active substance is docetaxel.

17. The nanocapsule system according to claim 10, wherein the active substance is a recombinant hepatitis B antigen (rHBsAg).

18. The nanocapsule system according to claim 10, wherein the active substance is a recombinant H1N1 influenza (HI) antigen.

19. A method for treating lung or pancreatic cancer in a subject in need thereof, the method comprising administering to said subject the nanocapsule system of claim 16, such that said lung or pancreatic cancer in said subject is treated.

20. A method for treating hepatitis B in a subject in need thereof, the method comprising administering to said subject the nanocapsule system of claim 17, such that said hepatitis B is treated or prevented.

21. A method for treating H1N1 influenza in a subject in need thereof, the method comprising administering to said subject the nanocapsule system of claim 18, such that said H1N1 influenza in said subject is treated or prevented.

22. A pharmaceutical composition comprising the nanocapsule system of claim 1 and one or more pharmaceutically acceptable excipients.

* * * * *